(12) United States Patent
Martin et al.

(10) Patent No.: US 12,090,337 B2
(45) Date of Patent: Sep. 17, 2024

(54) SYSTEMS AND METHODS FOR DETERMINING FLOW PARAMETERS OF ADMINISTERED FLUID FROM RADIOEMBOLIZATION DELIVERY DEVICE

(71) Applicant: Bard Peripheral Vascular, Inc., Tempe, AZ (US)

(72) Inventors: Adam Martin, Holly Springs, NC (US); Mircea Despa, Cary, NC (US); Michael D. Yarger, Chapel Hill, NC (US); Andrew Richards, Durham, NC (US); Casey Tyler Hebert, Tempe, AZ (US); Mark Nicholas Wright, Tempe, AZ (US); Brandon David Simmons, Tempe, AZ (US); Juergen Dorn, Neulußhem (DE)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 981 days.

(21) Appl. No.: 17/054,563

(22) PCT Filed: May 17, 2019

(86) PCT No.: PCT/US2019/032950
§ 371 (c)(1),
(2) Date: Nov. 11, 2020

(87) PCT Pub. No.: WO2019/222678
PCT Pub. Date: Nov. 21, 2019

(65) Prior Publication Data
US 2021/0128944 A1    May 6, 2021

Related U.S. Application Data

(60) Provisional application No. 62/673,628, filed on May 18, 2018, provisional application No. 62/673,632, filed on May 18, 2018.

(51) Int. Cl.
*A61N 5/10* (2006.01)
*A61B 18/00* (2006.01)
(Continued)

(52) U.S. Cl.
CPC .......... *A61N 5/1002* (2013.01); *A61M 5/172* (2013.01); *G16H 20/17* (2018.01); *G16H 20/40* (2018.01);
(Continued)

(58) Field of Classification Search
CPC .......... A61N 5/1002; A61N 2005/1021; A61N 5/1007; A61N 2005/1019;
(Continued)

(56) References Cited

U.S. PATENT DOCUMENTS 4,313,440 A    2/1982   Ashley
5,478,323 A    12/1995  Westwood et al.
(Continued)

FOREIGN PATENT DOCUMENTS

CN    101784295 A    7/2010
CN    101951975 A    1/2011
(Continued)

OTHER PUBLICATIONS

Chinese Office Action dated Sep. 5, 2022 pertaining to Chinese Application for Invention No. 201980040382.1 filed Dec. 16, 2020, pp. 1-20.
(Continued)

*Primary Examiner* — Thaddeus B Cox
*Assistant Examiner* — Joshua Daryl D Lannu
(74) *Attorney, Agent, or Firm* — Dinsmore & Shohl LLP; Ritu Singh

(57) ABSTRACT

Methods and systems for determination of flow parameters of administered fluid from a radioembolization delivery device may include translationally moving a device delivery
(Continued)

arm of the radioembolization delivery device in a translational direction, wherein the device delivery arm is coupled to a syringe holder such that move in the translational direction one of proximally or distally advances the syringe holder; sensing, via one or more pattern sensors, a corresponding movement of a pattern associated with the translational device delivery arm movement as a sensed pattern movement; generating, via the one or more pattern sensors, one or more output signals based on the sensed pattern movement; and generating, via a processor, a flow rate of the administered fluid, a flow amount of the administered fluid, and/or the translational direction of movement of the device delivery arm with respect to the syringe holder based on the one or more output signals.

23 Claims, 13 Drawing Sheets

(51) Int. Cl.
A61K 51/12 (2006.01)
A61M 5/00 (2006.01)
A61M 5/14 (2006.01)
A61M 5/142 (2006.01)
A61M 5/145 (2006.01)
A61M 5/168 (2006.01)
A61M 5/172 (2006.01)
A61M 5/178 (2006.01)
A61M 5/19 (2006.01)
A61M 5/20 (2006.01)
A61M 5/24 (2006.01)
A61M 5/315 (2006.01)
A61M 25/00 (2006.01)
A61M 25/01 (2006.01)
A61M 25/06 (2006.01)
A61M 39/10 (2006.01)
G16H 20/17 (2018.01)
G16H 20/40 (2018.01)
G16H 40/20 (2018.01)
G16H 40/63 (2018.01)

(52) U.S. Cl.
CPC ........... A61M 2205/3306 (2013.01); A61M 2205/3317 (2013.01); A61M 2205/3334 (2013.01); A61M 2205/502 (2013.01); A61M 2205/52 (2013.01); A61N 2005/1021 (2013.01)

(58) Field of Classification Search
CPC .... A61N 2005/1074; A61N 2005/1089; A61N 5/1001; A61M 5/172; A61M 2205/3306; A61M 2205/3317; A61M 2205/3334; A61M 2205/502; A61M 2205/52; A61M 2025/0004; A61M 5/1409; A61M 5/14216; A61M 5/1456; A61M 5/16809; A61M 5/1785; A61M 5/19; A61M 5/2448; A61M 25/0012; A61M 25/0082; A61M 25/0108; A61M 5/204; A61M 2005/1787; A61M 2005/2414; A61M 2005/247; A61M 2005/31598; A61M 2025/0031; A61M 2025/0036; A61M 2025/004; A61M 2025/0042; A61M 2202/0007; A61M 5/168; A61M 2025/0073; A61M 2025/0081; A61M 2025/0681; A61M 2039/1027; A61M 2039/1033; A61M 2039/1072; A61M 2205/32; A61M 2205/3327; A61M 2205/505; A61M 2205/8206; A61M 39/1011; A61M 5/14566; A61M 25/0068; A61M 25/0071; A61M 39/10; G16H 20/17; G16H 20/40; G16H 40/20; G16H 40/63; A61B 2018/00529; A61K 51/1244; A61K 51/1251

See application file for complete search history.

(56) References Cited

U.S. PATENT DOCUMENTS

| | | | |
|---|---|---|---|
| 5,496,284 A | 3/1996 | Waldenburg | |
| 6,152,913 A | 11/2000 | Feith et al. | |
| 6,508,807 B1 | 1/2003 | Peters | |
| 6,606,370 B1 | 8/2003 | Kasprowicz | |
| 6,723,074 B1 | 4/2004 | Halseth | |
| 7,713,239 B2 | 5/2010 | Uber, III et al. | |
| 2001/0021826 A1 | 9/2001 | Winkler | |
| 2003/0201639 A1 | 10/2003 | Korkor | |
| 2003/0229311 A1* | 12/2003 | G. Morris | A61M 5/1456 604/151 |
| 2004/0111078 A1 | 6/2004 | Miyahara | |
| 2004/0258614 A1 | 12/2004 | Line et al. | |
| 2005/0085685 A1 | 4/2005 | Barbut | |
| 2006/0033334 A1 | 2/2006 | Weber et al. | |
| 2006/0091329 A1 | 5/2006 | Eguchi | |
| 2006/0293552 A1 | 12/2006 | Polsinelli et al. | |
| 2007/0129591 A1 | 6/2007 | Yanke et al. | |
| 2007/0141339 A1 | 6/2007 | Song et al. | |
| 2008/0058719 A1 | 3/2008 | Edwards et al. | |
| 2008/0103564 A1 | 5/2008 | Burkinshaw et al. | |
| 2008/0200747 A1 | 8/2008 | Wagner et al. | |
| 2009/0018498 A1 | 1/2009 | Chiu et al. | |
| 2009/0092677 A1 | 4/2009 | Richard | |
| 2009/0232586 A1 | 9/2009 | Diodati et al. | |
| 2010/0063481 A1 | 3/2010 | Hoffman | |
| 2010/0084585 A1 | 4/2010 | Prosser | |
| 2012/0190976 A1 | 7/2012 | Kleinstreuer | |
| 2012/0201726 A1 | 8/2012 | Pearcy et al. | |
| 2013/0165899 A1 | 6/2013 | Haueter et al. | |
| 2013/0317277 A1 | 11/2013 | Lemer | |
| 2014/0046295 A1 | 2/2014 | Uber, III et al. | |
| 2014/0088556 A1 | 3/2014 | Makaveev et al. | |
| 2014/0163302 A1 | 6/2014 | Fox et al. | |
| 2014/0207178 A1 | 7/2014 | Chomas et al. | |
| 2014/0236093 A1 | 8/2014 | Eggert et al. | |
| 2014/0257233 A1 | 9/2014 | Cowan | |
| 2015/0273089 A1 | 10/2015 | Gray | |
| 2015/0285282 A1 | 10/2015 | Weitz et al. | |
| 2016/0325047 A1 | 11/2016 | Vedrine et al. | |
| 2016/0331853 A1 | 11/2016 | Taub | |
| 2016/0331998 A1 | 11/2016 | Hoffman et al. | |
| 2017/0065732 A1 | 3/2017 | Srinivas et al. | |
| 2017/0120032 A1 | 5/2017 | Miyazaki et al. | |
| 2017/0151357 A1 | 6/2017 | Cade | |
| 2017/0189569 A1 | 7/2017 | Souresrafil et al. | |
| 2017/0238951 A1 | 8/2017 | Yang et al. | |
| 2017/0304151 A1 | 10/2017 | Van Den Berg et al. | |

FOREIGN PATENT DOCUMENTS

| | | | |
|---|---|---|---|
| CN | 105025975 A | 11/2015 | |
| CN | 105163775 A | 12/2015 | |
| DE | 3035290 A1 | 4/1982 | |
| DE | 4318101 A1 | 12/1994 | |
| EP | 2179758 A2 | 4/2010 | |
| FR | 2917981 A1 | 1/2009 | |
| JP | 2006017660 A | 1/2006 | |
| JP | 2006116170 A | 5/2006 | |
| WO | 2007008511 A2 | 1/2007 | |
| WO | 2009026060 A2 | 2/2009 | |
| WO | 2009039203 A2 | 3/2009 | |
| WO | 2009039214 A2 | 3/2009 | |
| WO | WO-2011014562 A1 * | 2/2011 | ....... A61B 17/12109 |
| WO | 2012006555 A1 | 1/2012 | |
| WO | 2012118687 A1 | 9/2012 | |
| WO | 2013153722 A1 | 10/2013 | |

(56) References Cited

FOREIGN PATENT DOCUMENTS

| | | |
|---|---|---|
| WO | 2014124424 A1 | 8/2014 |
| WO | 2014137980 A1 | 9/2014 |
| WO | 2014165058 A1 | 10/2014 |
| WO | 2016049685 A1 | 4/2016 |
| WO | WO-2016161346 A1 * 10/2016 .......... A61M 5/1452 |
| WO | 2017053398 A1 | 3/2017 |
| WO | 2017157974 A1 | 9/2017 |
| WO | 2019006099 A1 | 1/2019 |

OTHER PUBLICATIONS

Japanese Office Action dated Apr. 21, 2023 pertaining to Japanese application No. 2020-564526 filed Nov. 17, 2020, pp. 1-8.

Evidence 1: "SIFIC Hospital Infection Prevention and Control Supplies Guidelines 2014-2015", Hu Bijie et al., p. 233, Shanghai Science and Technology Press, May 2014.

Evidence 2: "Clinical Nursing Teaching in Internal Medicine", Wang Xining et al., p. 113, Tianjin Science and Technology Translation and Publishing Company, Aug. 2010.

Office Action dated Apr. 19, 2023 pertaining to Chinese Application 201980042280.3.

Office Action dated Apr. 10, 2023 pertaining to JP Patent Application No. 2020-564531.

Chiesa, C. et al.; A dosimetric treatment planning strategy in radioembolization of hepatocarcinoma with 90Y glass microspheres; The Quarterly Journal of Nuclear Medicine and Molecular Imaging, vol. 56, No. 6; Dec. 1, 2012.

Chiesa, C. et al.; Radioembolization of hepatocarcinoma with 90Y glass microspheres: development of an individualized treatment planning strategy based on dosimetry and radiobiology; European Journal of Nuclear Medicine and Molecular Imaging, Springer Verlag, Heidelberg, DE; vol. 42; No. 11; Jun. 27, 2015.

Spreafico, C. et al.; The dosimetric importance of the number of 90Y microspheres in liver transarterial radioembolizaiton (TARE); European Journal of Nuclear Medicine and Molecular Imaging, Springer Verlag, Heidelberg, DE; vol. 41, No. 4; Jan. 30, 2014.

International Search Report and Written Opinion dated Aug. 1, 2019 pertaining to International Application No. PCT/US2019/032983.

International Search Report and Written Opinion dated Dec. 13, 2019 pertaining to International Application No. PCT/US2019/032987.

International Search Report and Written Opinion dated Oct. 16, 2019 pertaining to International Application No. PCT/US2019/032955.

International Search Report and Written Opinion dated Jul. 23, 2019 pertaining to International Application No. PCT/US2019/032950.

International Search Report and Written Opinion dated Sep. 24, 2019 pertaining to International Application No. PCT/US2019/033011.

International Search Report and Written Opinion dated Jul. 26, 2019 pertaining to International Application No. PCT/US2019/032965.

International Search Report and Written Opinion dated Jul. 29, 2019 pertaining to International Application No. PCT/US2019/032954.

International Search Report and Written Opinion dated Aug. 7, 2019 pertaining to International Application No. PCT/US2019/032986.

Arepally, A.; Quantification and Reduction of Reflux during Embolotherapy Using an Antireflux Catheter and Tantalum Microspheres: Ex Vivo Analysis; J Vasc Interv Radiol; 2013; 24:575-580.

Chung, J. et al.; Novel use of the Surefire antireflux device in subtotal splenic embolization; Journal of Vascular Surgery Cases; Dec. 1, 2015; pp. 242-245; vol. 1, No. 4.

Ho, S. et al; Clinical evaluation of the partition model for estimating radiation doses from yttrium-90 microspheres in the treatment of hepatic cancer; European Journal of Nuclear Medicine, Springer, Berlin, Heidelberg, DE: vol. 24. No. 3; Mar. 1, 1997.

Hospital Clinics et al.; Y-90 MicroSpheres (SIRSpheres) for treatment of hepatocellular carcinoma; Mar. 1, 2017.

Morshedi, M. et al.; Yttrium-90 Resin Microsphere Radioembolization Using an Antireflux Catheter: An Alternative to Traditional Coil Embolization for Nontarget Protection; Cardiovasc Intervent Radiol; 2015; 38:381-38; Springer.

Sirtex Medical Limited: Sirtex Medical Products Pty Ltd SIR-Spheres (Ytttrium-90 Microspheres); Apr. 1, 2005.

Theragenics Corp.; Therasphere IDOC TM; Aug. 4, 2015.

Tong, A. et al; Yttrium-90 hepatic radioembolization: clinical review and current techniques in interventional radiology and personalized dosimetry; British Journal of Radiology; vol. 89, No. 1062; Jun. 1, 2016.

US FDA; Theresphere IDOC—Humanitarian Device Exemption (HDE); Sep. 14, 2015.

Westcott, M. et al.; The development, commercialization, and clinical context of yttrium-90 radiolabeled resin and glass microspheres; Advances in Radiation Oncology; 2016; vol. 1; pp. 351-364.

Sirtex Medical Limited; SMAC-SIR-Spheres Microspheres Activity Calculator; May 6, 2018.

* cited by examiner

SYSTEMS AND METHODS FOR DETERMINING FLOW PARAMETERS OF ADMINISTERED FLUID FROM RADIOEMBOLIZATION DELIVERY DEVICE

CROSS-REFERENCE TO RELATED APPLICATIONS

This application is a U.S. National Phase of International Application No. PCT/US2019/032950, entitled "SYSTEMS AND METHODS FOR DETERMINING FLOW PARAMETERS OF ADMINISTERED FLUID FROM RADIOEMBOLIZATION DELIVERY DEVICE" and filed May 17, 2019, which claims the benefit of U.S. Provisional Pat. App. No. 62/673,628, entitled "DUAL-STAGE SYRINGES WITH LOCKING MECHANISM," and filed on May 18, 2018, and U.S. Provisional Pat. App. No. 62/673,632, entitled "RADIOEMBOLIZATION DELIVERY DEVICE," and filed on May 18, 2018, the entireties of which are incorporated by reference herein.

TECHNICAL FIELD

The present specification generally relates to medical devices for treating cancer, and more particularly to medical devices configured and operable to deliver radioactive compounds to a treatment area within a patient's body in procedures such as transarterial radioembolization and determination of flow parameters of administered fluid from such radioembolization delivery devices.

BACKGROUND

In cancer treatments involving radiation therapy, inadvertent or excess exposure to radiation from radioactive therapeutic agents can be harmful and potentially lethal to patients or medical personnel. Accordingly, medical instruments for radiation therapies must be configured to localize the delivery of radioactive material to a particular area of the patient's body while shielding others from unnecessarily being exposed to radiation.

Transarterial radioembolization is a transcatheter intra-arterial procedure performed by interventional radiology and is commonly employed for the treatment of malignant tumors. During this medical procedure, a microcatheter is navigated into a patient's liver where radioembolizing microspheres loaded with a radioactive compound, such as yttrium-90 ($^{90}Y$), are delivered to the targeted tumors. The microspheres embolize blood vessels that supply the tumors while also delivering radiation to kill tumor cells.

Generally, medical devices for performing radioembolization procedures require multiple syringes, external tubing, a vial containing the radioactive compound, and a bulky shield assembly for containing and shielding the radioactive vial. Such devices typically involve time consuming and labor-intensive setup procedures. The complex devices are commonly stationary and thereby limit a physician's mobility in an operating room to within a certain proximity of the device.

Routine manipulation of a product container storing radioactive material during radioembolization procedures generally requires a Nuclear Medicine Technician, who handles the material with forceps or tweezers. This process involves further potential of exposing additional medical personnel to radioactivity, and contaminating the operating room. Syringes for manually administering the radioactive compound as an administered fluid are prone to inconsistent flow rates and pressures. Insufficient injection rates result in decreased bead dispersion, which may impact efficacy of the treatment.

Accordingly, a need exists for a medical device that is configured and operable to perform radioembolization that incorporates a simplistic design and consistent means for administering and monitoring constant flow rates and pressure of the radioactive compound to the patient's body. A simplified device provides a physician enhanced maneuverability in the operating room during the medical procedure, including an ability to reposition the device about the patient as desired. Additionally, a device with enhanced shielding of the radioactive material enables greater protection to a physician utilizing the medical device while treating a patient.

SUMMARY

In one embodiment, a method for determination of flow parameters of administered fluid from a radioembolization delivery device may include translationally moving a device delivery arm of the radioembolization delivery device in a translational direction. The device delivery arm may be coupled to a syringe holder such that movement in the translational direction one of proximally or distally advances the syringe holder. The method may further include sensing, via one or more pattern sensors, a corresponding movement of a pattern associated with the translational device delivery arm movement as a sensed pattern movement, generating, via the one or more pattern sensors, one or more output signals based on the sensed pattern movement, and generating, via a processor, at least one of a flow rate of the administered fluid, a flow amount of the administered fluid, or the translational direction of movement of the device delivery arm with respect to the syringe holder based on the one or more output signals.

In another embodiment, a system for determination of flow parameters of administered fluid from a radioembolization delivery device may include a radioembolization delivery device including a device delivery arm coupled to a syringe holder, a pattern assembly, and one or more pattern sensors configured to detect the pattern assembly based on movement of the pattern assembly, and the device delivery arm configured to move in a translational direction to one of proximally or distally advance the syringe holder, and a processor communicatively coupled to the radioembolization delivery device and a non-transitory computer storage medium. The non-transitory computer storage medium stores instructions that, when executed by the processor, cause the processor to: monitor translational movement of the device delivery arm of the radioembolization delivery device in the translational direction; sense, via the one or more pattern sensors, a corresponding movement of the pattern assembly associated with the translational device delivery arm movement as a sensed pattern movement; generate, via the one or more pattern sensors, one or more output signals based on the sensed pattern movement; and generate at least one of a flow rate of the administered fluid, a flow amount of the administered fluid, or a direction of movement of the device delivery arm with respect to the syringe holder based on the one or more output signals.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
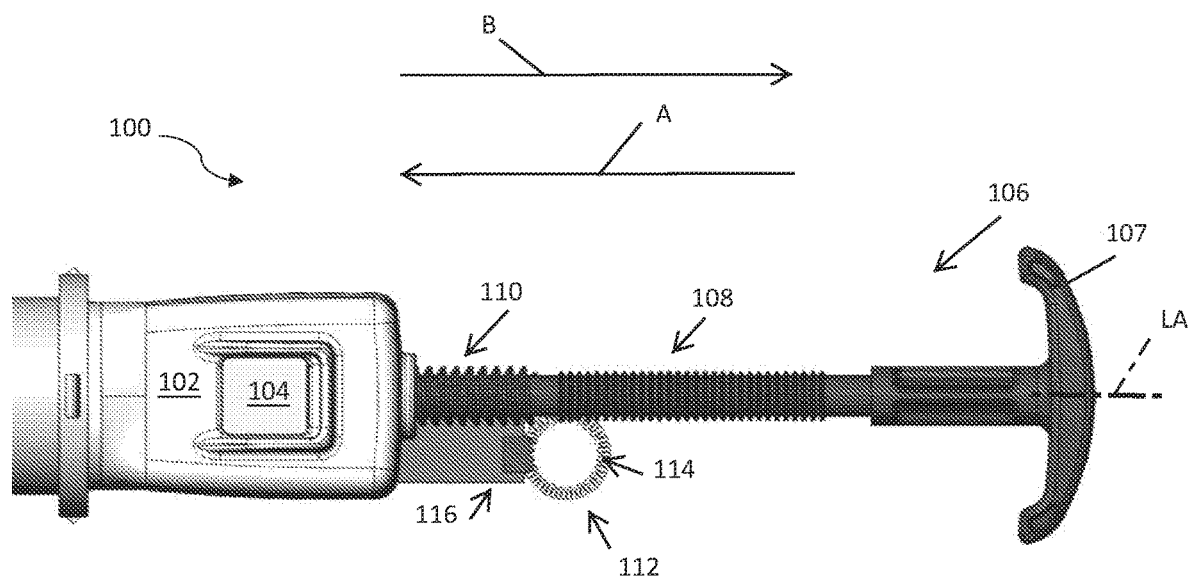
FIG. 1A illustrates a side view of a radioembolization delivery device with a translational and/or rotational plunger to administer therapeutic fluid, according to one or more embodiments shown and described herein.

Referring generally to the figures, embodiments of the present disclosure are directed to systems and methods for determination of flow parameters of administered fluid from radioembolization delivery devices as described herein. Various embodiments of such systems and methods are described in detail herein.

Radioembolization involves a combination of (1) radiation therapy using ionizing radiation to kill cancer cells and shrink tumors and (2) an embolization procedure to occlude blood vessels feeding a tumor and thus to treat, for example, cancer of the liver. Radioembolization is directed to placement of a radioactive material directly inside a patient body, which form of treatment is called internal rational therapy. In radioembolization, tiny glass or resin beads called microspheres (or spheres) are placed inside blood vessels feeding a tumor to block (e.g., occlude) the supply of blood to cancer cells. Once the microspheres filled with the radioactive isotope yttrium Y-90 become lodged at a tumor site, the lodged microspheres deliver a high dose of radiation to the tumor and not to normal tissues. Delivery of microspheres including mixing of the microspheres with a diluent, which is injected as an administered fluid into a patient using a syringe-holder delivery apparatus, such as described in U.S. Provisional Pat. App. Nos. 62/673,628 and 62/673,632, each of which is incorporated by referenced herein and above. An administration flow rate that equals a vascular flow rate of a subject is generally desired, and a flow rate may be estimated by a clinician performing the radioembolization procedure. The clinician may further manually keep track of a number of boluses administered through the procedure to determine a total volume.

The embodiments described herein are directed to radioembolization delivery devices including pattern sensor assemblies to sense one or more patterns within the delivery devices to generate pattern signals from which to automatically generate and determine flow parameters such as flow rate of a therapeutic fluid, flow amount of the therapeutic fluid, and/or a direction of travel of a device delivery arm coupled to the syringe holder that administers the therapeutic fluid. Thus, the embodiments described herein aid in the therapeutic fluid delivery procedure by determining and displaying information of a volumetric flow rate an a total infused volume through use of non-invasive pattern sensors removed from a fluid path and configured to determine a syringe plunger position and actuation direction during the administration procedure, as described in greater detail further below. The device delivery arm may translate to advance the syringe to administer fluid, whether through a direct translation or through a rotation that effects a translation, where such translation and/or rotation may be monitored by the sensors and/or systems described herein. Further, corresponding direction and/or speed of travel of the delivery device arm based on the monitored information may be displayed through the systems described herein. The delivery device arm and/or pattern sensor embodiments described herein include one or more technical effects directed to high reliability, increased accuracy, and low energy consumption based on pattern detection from alternating set sequences to determine output parameters, such a measurement of a change of liquid volume in a syringe based on a sensed pattern indicating movement in a distal direction to advance the syringe, as described in one or more embodiments herein.

In embodiments, attachment of a gear to a threaded plunger (e.g., a device delivery arm) that also includes a ring portion having a plurality of spaced rings in a pattern assists to sense rotational direction and distance via a quadrature encoder to determine a stopper position and velocity to calculate flowrate. Referring to FIG. 1A, a radioembolization delivery device 100 with a translational and/or rotational plunger to administer therapeutic fluid, such as a radioactive compound for a radioembolization procedure, is shown. The radioembolization delivery device 100 includes a device delivery arm 106 configured to translationally (e.g., linearly) move in a direction of an arrow A or of an arrow B, opposite to the arrow A, along a longitudinal axis LA of the device delivery arm 106 of the radioembolization delivery device 100. The device delivery arm 106 may be coupled to a syringe holder (not shown but disposed within a housing 102 of the radioembolization delivery device 100) such that movement in the translational direction one of proximally or distally advances the syringe holder. The radioembolization delivery devices 100, 200, 300, 400, 500, 600 described herein similarly may affect a translational motion in either the direction of the arrow A or the arrow B along the longitudinal axis LA of the respective device delivery arms 106, 206, 306, 406, 506, 606, as well as a counter-clockwise or a clockwise rotation around the respective longitudinal axis LA. The radioembolization delivery devices 700, 800, 900, 1000 described herein similarly may affect a translational motion in either the direction of the arrow A or the arrow B along the longitudinal axis LA of the respective device delivery arms 706, 806, 906, 1006, as will be described in greater detail further below.

The device delivery arm 106 of the radioembolization delivery device 100 may further be configured to rotate about the longitudinal axis LA. The device delivery arm 106 may include a handle 107, a ring portion 108, and a threaded portion 110. In embodiments, the device delivery arm 106 may be approximately twice a length of the threaded portion 110, and a housing may include a support board, sensors, as the like as described herein. Further, the device delivery arm 106 may include a button 104 configured to allow for direct translation movement without rotation of device delivery arm 106 upon being pressed. As a non-limiting example, pressure upon the button 104 may unlatch an internal feature from the threaded portion 110, allowing the threaded portion 110 to glide past an internal surface of the housing 102 such the device delivery arm 106 does not require a rotation to affect a translational motion.

Figure 1B:
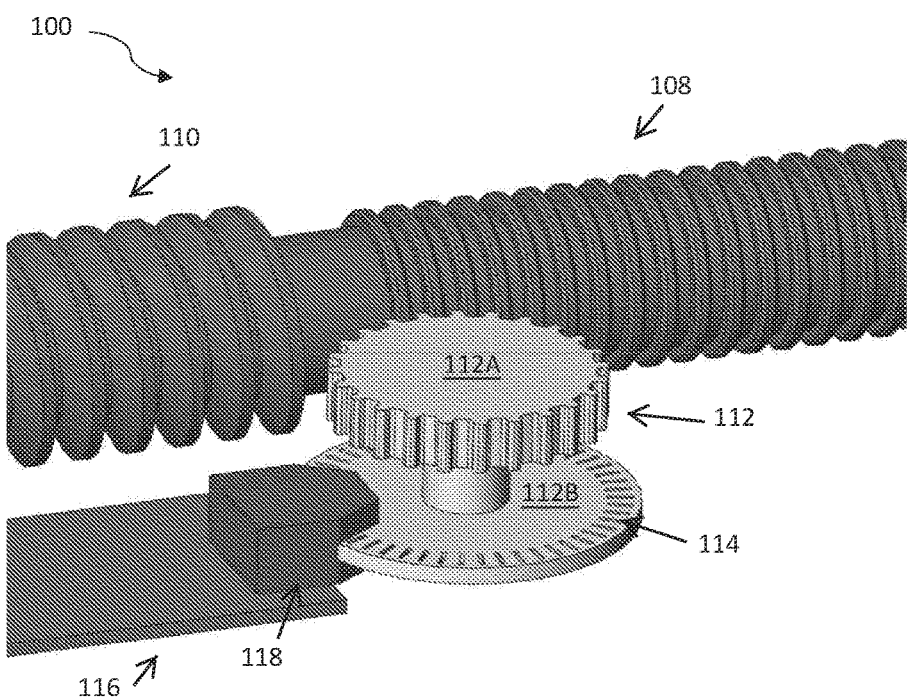
FIG. 1B is a side perspective view of a gear assembly of the device of FIG. 1A, according to one or more embodiments shown and described herein.

Referring to FIG. 1B, the ring portion 108 includes a ring pattern formed through a series of spaced apart ring features projecting from the device delivery arm 106 at a set pattern with a spacing distance width between adjacent rings. A gear assembly 112 is configured to detect the ring pattern of the ring portion 108 through a tooth connection of the gear assembly 112 with each projecting ring feature to turn a top gear 112A and effect a corresponding rotation of a rotary wheel encoder 112B coupled to the top gear 112A. The rotary wheel encoder 112B includes a pattern 114 that is sensed by a pattern sensor that may be disposed in a clamp 118 of a support board 116 configured to hold the gear assembly 112 in a position in the radioembolization delivery device 100. Translation of the device delivery arm 106 in the direction of the arrow A turns the top gear 112A in a counter-clockwise direction, while translation of the device delivery arm 106 in the direction of the arrow B turns the top gear 112A in a clock-wise direction.

Figure 2A:
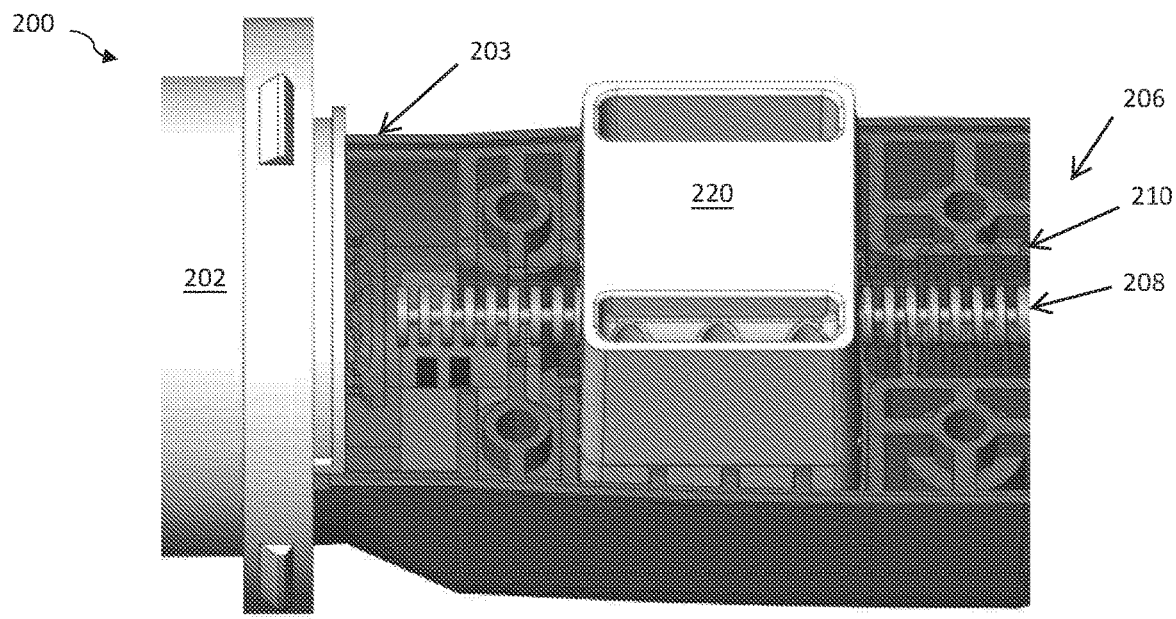
FIG. 2A is a partially exposed, side perspective view of another radioembolization delivery device with a translational and/or rotational plunger to administer therapeutic fluid, according to one or more embodiments shown and described herein.
Figure 2B:
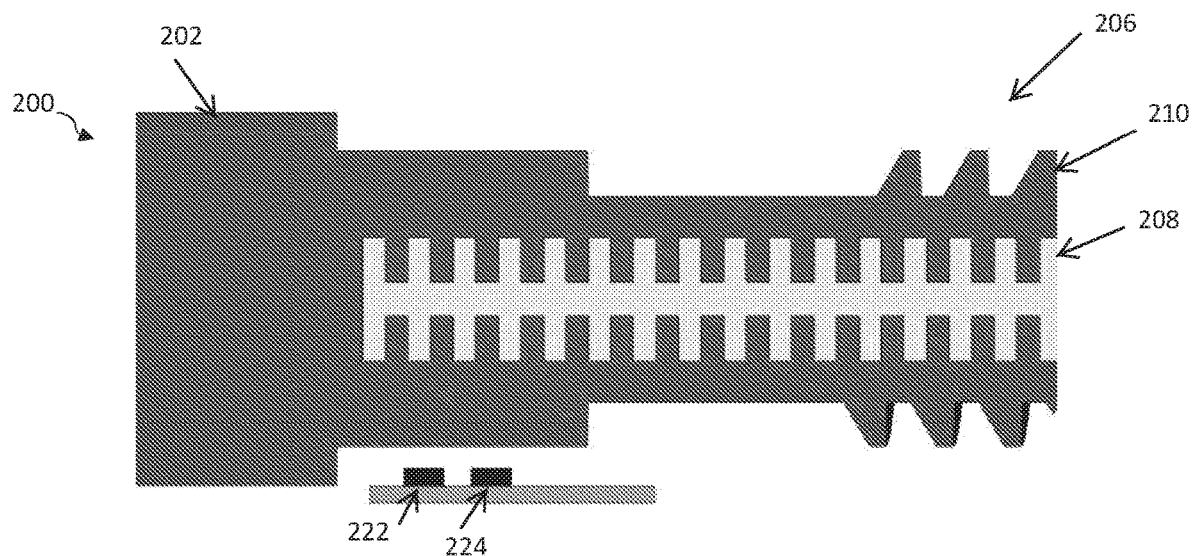
FIG. 2B is a side plan, cross-sectional view of a ring assembly of the device of FIG. 2A, according to one or more embodiments shown and described herein.

In some aspects, a ferrous object is embedded in a plunger rod (e.g., the device delivery arm) and sensors are placed and configured to sense variations in volume of the ferrous object as the ferrous object translates, which changes a level of a signal response to track a corresponding pattern in the translating ferrous object. Based on the order and frequency of the signal level changes, a direction and linear velocity of the device delivery arm including the embedded ferrous object may be determined. Referring to FIG. 2A, a radioembolization delivery device 200 includes a device delivery arm 206 projecting from a housing 202, disposed in an arm enclosure 203, and held therein via a clamp 220. The device delivery arm 206 includes a ring portion 208 embedded within a threaded portion 210, as shown in FIG. 2B. Pattern sensors 222, 224 configured to detect a pattern of the ring portion 208 are disposed to face the ring portion 208.

The ring portion 208 may be made of a magnetic or ferrous object disposed within the device delivery arm 206 and configured to be sensed by the pattern sensors 222, 224. The ring portion 208 may include a ball bearing and/or pattern rode disposed in a center of the device delivery arm 206 with inductive sensors disposed on an exterior of the device delivery arm 206. Additionally or alternatively, the pattern sensors may be Hall effect sensors configured to measure a magnitude of a magnetic field associated with sensed portions of the ring portion 208 to sense a detected pattern of the ring portion 208. A pair of reflective sensor components may be disposed opposite the pattern sensors 222, 224 to reflect back a transmitted signal. The pattern sensors 222, 224 may be disposed on and coupled to a printed circuit board configured to sense output signals from the pattern sensors 222, 224 with respect to the detected pattern of the ring portion 208.

An output voltage of a Hall effect sensor is directly proportional to a magnetic field strength through the Hall effect sensor, and a proximal magnetic or ferrous material, such as a projecting ring of the ring portion 208, would cause a different magnetic field detection by a Hall effect sensor than a gap between a pair of projection rings of the ring portion 208. By the sensing of one of the pattern sensors 222, 224 of a projecting ring and the sensing of the other of the pattern sensors 222, 224 of a gap between projecting rings, where a spacing between the projecting rings of the ring portion 208 is known, a direction of travel and amount traveled may be generated and used to generate associated flow parameters for fluid administration by the radioembolization delivery device 200. In contrast to inductive sensors, which respond to a dynamic magnetic field that induces a current in a coil of wire to produce a voltage output, Hall effect sensors detect static magnetic fields through a thin metal strip having an applied current such that, in the presence of a magnetic field, the electrons in the thin metal strip deflect to an edge and produce a voltage gradient perpendicular to a feed current.

While Hall effect sensors are described as an embodiment of the pattern sensors 222, 224, it is contemplated and within the scope of this disclosure that inductive sensors, optical sensors, switch-sensors, magnetic sensors, and the like may be used to sense the ring pattern of the ring portion 208 of FIG. 2B. By way of example, and not as a limitation, the pattern sensors 222, 224 may be optical sensors configured to detect a different light reflectivity associated with each projecting ring and each gap between projecting rings of the ring portion 108. In embodiments, an external placement of the ring portion 108 may also be detected by the pattern sensors 222, 224 may be optical sensors as one or more optical sensors configured to detect an external pattern including a projecting and a gap and a predetermined distance disposed therebetween.

Figure 3A:
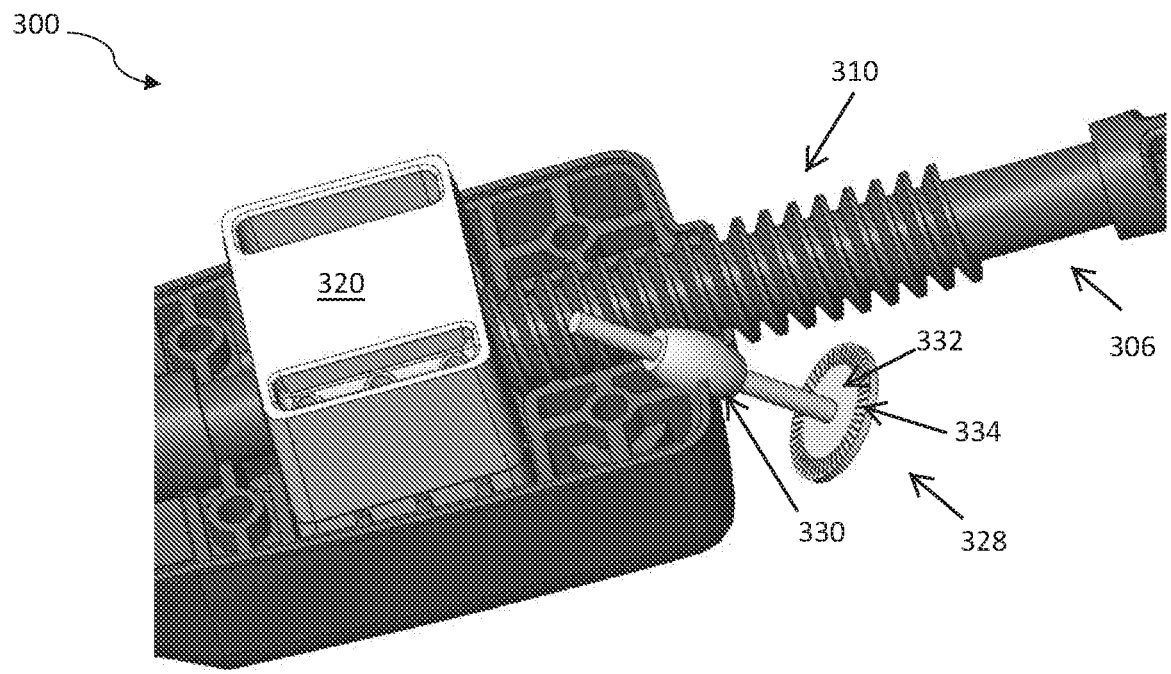
FIG. 3A is a partially exposed, side perspective view of another radioembolization delivery device with a translational and/or rotational plunger to administer therapeutic fluid, according to one or more embodiments shown and described herein.
Figure 3B:
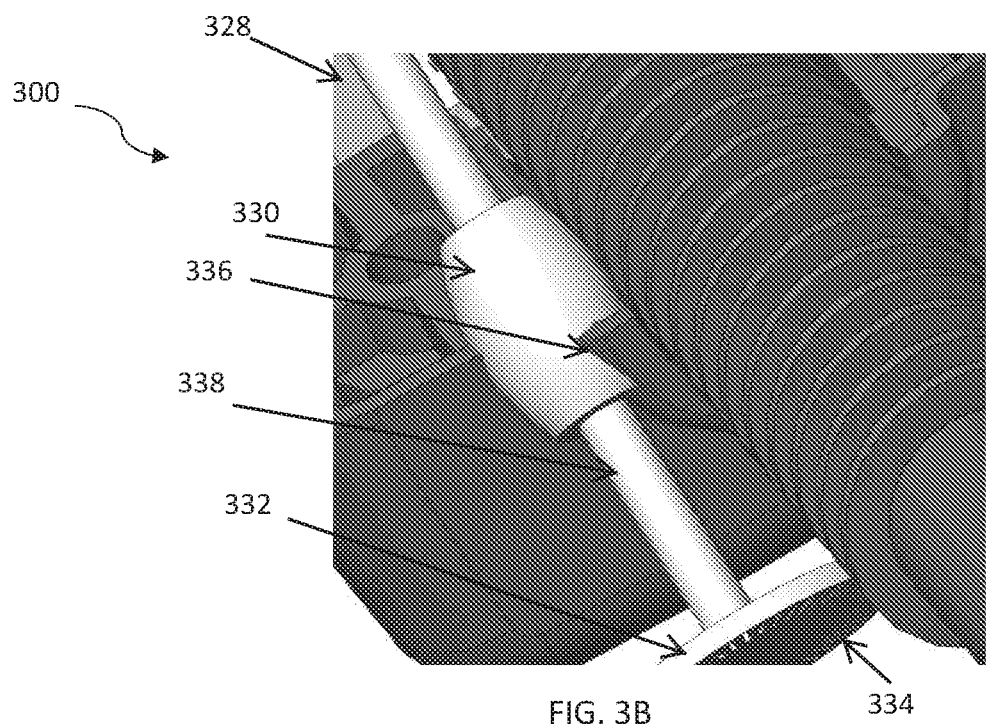
FIG. 3B is a top perspective view of an omni wheel assembly of the device of FIG. 3A, according to one or more embodiments shown and described herein.

In an embodiment, an encoded wheel or one or more cylinders may engage with a device delivery arm surface to sense a rotational and translation motion of the device delivery arm, and both motions may be sensed through a single omni wheel assembly. Referring to FIGS. 3A-3B, a radioembolization delivery device 300 including an omni wheel assembly 328 is shown. The omni wheel assembly 328 is configured to engage with a surface of a threaded portion 310 of the device delivery arm 306 such that a translation motion the device delivery arm 306 rotate an omni wheel 330 of the omni wheel assembly 328, which effects through connection via a rod 338 a corresponding rotation of an encoder wheel 332 including a pattern 334 that is sensed by at least one pattern sensor (not shown). In embodiments, the device delivery arm 306 is contained within a housing of the radioembolization delivery device 300 through a clamp 320, and the omni wheel assembly 328 is contained within the housing through a clamp 336. Rotation of the omni wheel assembly 328 effecting a rotation of the encoder wheel 332 in turned causes a rotation of the pattern 334 of the encoder wheel 332 that is sensed by at least one pattern sensor, which may be an optical wheel sensor, an inductive sensor, a capacitance sensor, and the like to detect the pattern 334 and generate a flow rate, flow amount, and direction of travel based on the detected pattern 334.

Figure 4A:
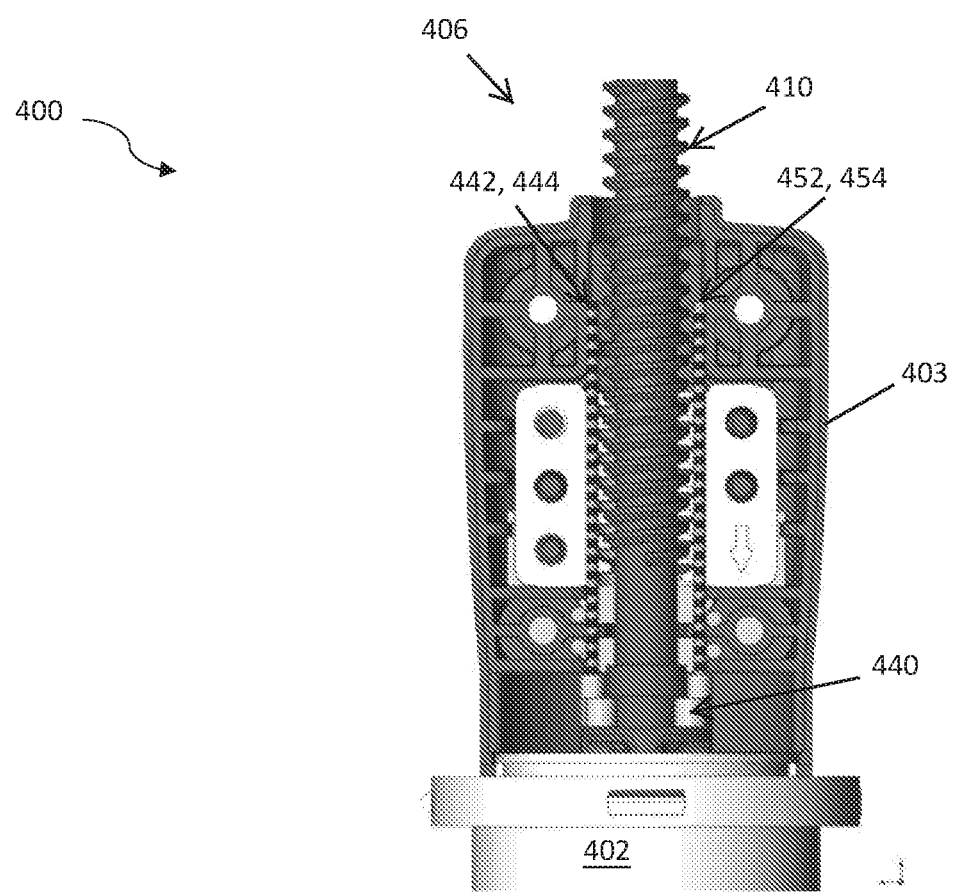
FIG. 4A is a partially exposed, side view of another radioembolization delivery device with a translational and/or rotational plunger to administer therapeutic fluid, according to one or more embodiments shown and described herein.
Figure 4B:
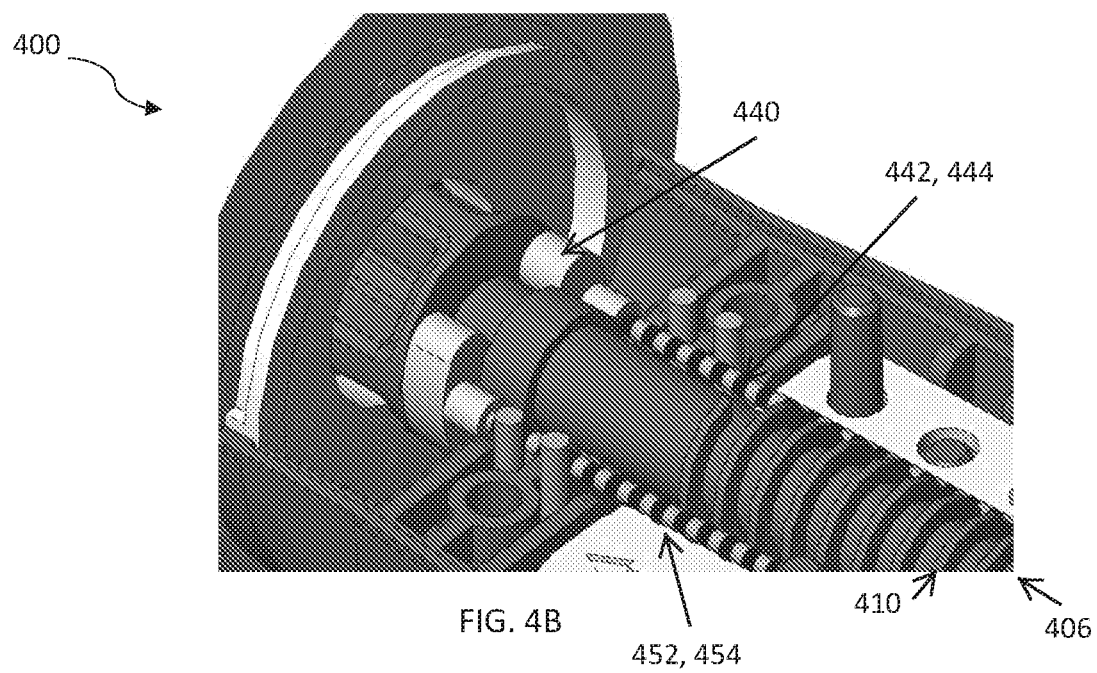
FIG. 4B is a top-side perspective view of a conductive rod assembly of the device of FIG. 4A, according to one or more embodiments shown and described herein.
Figure 4C:
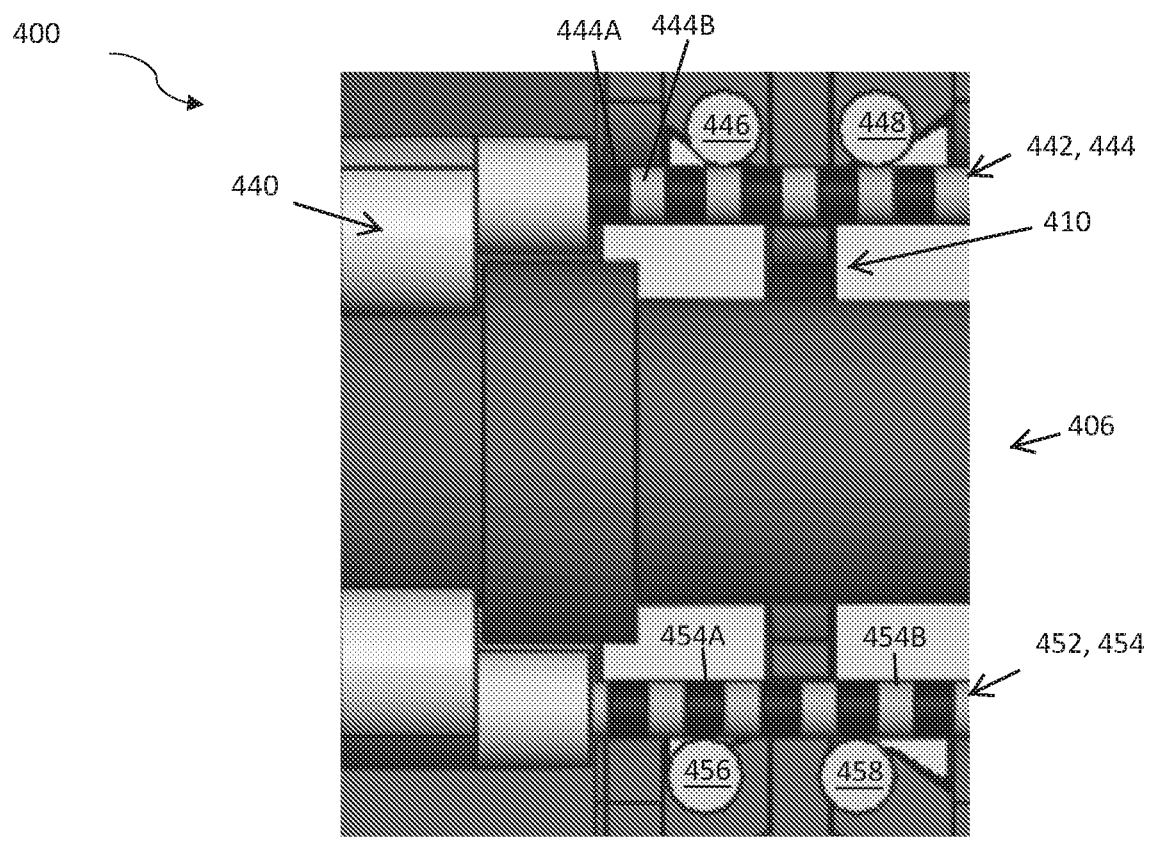
FIG. 4C is a top view of the conductive rod assembly of FIG. 4B, according to one or more embodiments shown and described herein.

In embodiments, encoding of conductive rods that connect to a circuit and act as an electrical switch assist to determine a sensed pattern. The rods may be connected to a collar feature that is free to rotate about a center axis as the device delivery arm is rotated to keep the rods in a sensing area. As the device delivery arm translates either by a lead or axial load, the rods close the electrical circuit. Through the generated order and frequency of switching information, a direction and linear velocity of the device delivery arm may be determined. Referring to FIGS. 4A-4C, a radioembolization delivery device 400 includes a conductive rod assembly including a pair of conductive rods 442, 452 projecting from a clip feature 440 disposed about the device delivery arm 406 extending from a housing 402 and disposed in an enclosure 403. The clip feature 440 may be a slip ring or other fastening to attached the pair of conductive rods 442, 452 to the device delivery arm 406 such that the pair of conductive rods 442, 452 move together with the device delivery arm 406 while rotation of the delivery arm 406 does not cause a rotation of the clip feature 440 or the pair of conductive rods 442, 452. The device delivery arm 406 includes a threaded portion 410 and is configured for rotational and/or translational movement along and about a longitudinal axis of the device delivery arm 406. The conductive rod 442 includes an alternating pattern 444, and the conductive rod 452 includes an alternating pattern 454.

Referring to FIG. 4C, the alternating pattern 444 includes a high feature 444A and a low feature 444B detected by lead switches 446, 448 upon contact. Similar, the alternating pattern 454 includes a high feature 454A and a low feature 454B detected by lead switches 456, 458. The lead switches 446, 448, 456, 458 may include electrical contacts such as metal plate switches configured to contact the alternating patterns to be switch on and off per high and low readings as described herein. The lead switch detection may result in an on/off wave form that follows a binary model and forms a step-like wave form. In embodiments, the alternating patterns 444, 454 may be sensed by one or more other pattern sensors including, but not limited to, Hall effect sensors, magnetic sensors, optical sensors, and the like and may generate a range of non-binary signals to form a sine-like wave form. The pattern sensors may detect quadrature signals disposed 90 degrees apart from the alternating patterns 444, 454. As a non-limiting example, when the lead switch 446 contacts a low feature 444B of the alternating pattern 444 indicative of a closed switch, the opposing lead switch 456 contacts a high feature 454A of the alternating pattern 454 indicative of an open switch.

Figure 5A:
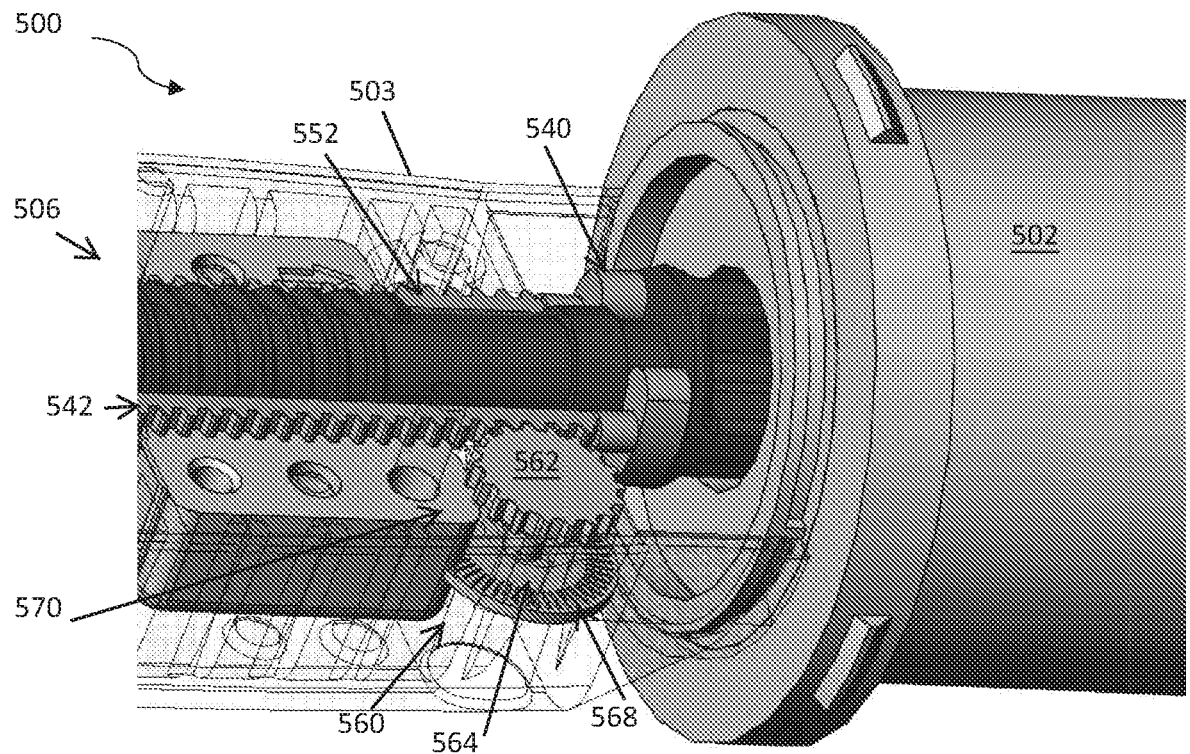
FIG. 5A is a partially exposed, side perspective view of another radioembolization delivery device with a translational and/or rotational plunger to administer therapeutic fluid, according to one or more embodiments shown and described herein.
Figure 5B:
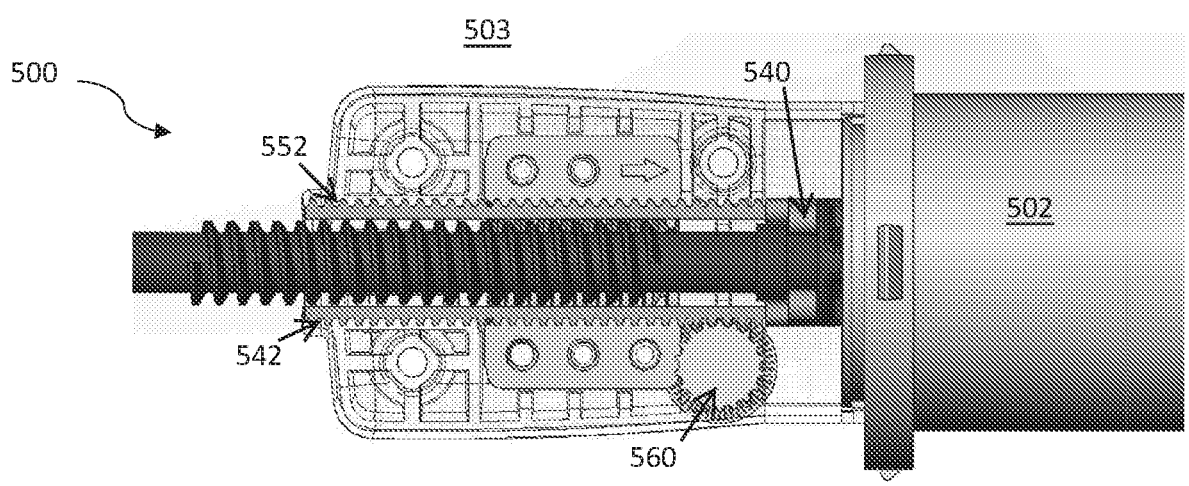
FIG. 5B is a side view of a rack and pinion rod assembly of the device of FIG. 5A, according to one or more embodiments shown and described herein.

In an embodiment, an encoded rack and pinion assembly includes a pinion attached to a rotary quadrature encoder and a rack attached to a translating device delivery arm via a collar feature that is not constrained to the rotation of the device delivery arm. Thus, the collar feature prevents the rack and pinion assembly from rotating while allowing for a translation free as the device delivery arm is rotated and/or translated. Referring to FIGS. 5A-5B, a radioembolization delivery device 500 is shown that includes a rack and pinion rod assembly 560 that includes a pinion 562 rotatable by movement of a rack 542 in a translational direction and attached to a rotary encoder 564 including a pattern 568 configured for detection by a sensor (not shown). The radioembolization delivery device 500 includes a device delivery arm 506 extending from a housing 502 and enclosed in an enclosure 503 including clamps 570 to contain internal components. A pair of rack rods are disposed on opposite sides of the device delivery arm 506 and extend from a clip feature 540 disposed about the device delivery arm 506. A rotation of the device delivery arm 506 does not effect a corresponding rotation of the clip feature 540 such that the rack rods 542, 552 do not rotate but rather only translate along with the device delivery arm 506. The projecting teeth of the rack rod 542 inserted into grooves of the pinion 562 may generate one of a high-low pattern, while the gaps between the projecting teeth of the rack rod 542 receiving teeth of the pinion 562 may generate the other of the high-low pattern to generate a flow rate, flow amount, and direction of motion of the device delivery arm 506.

Figure 6:
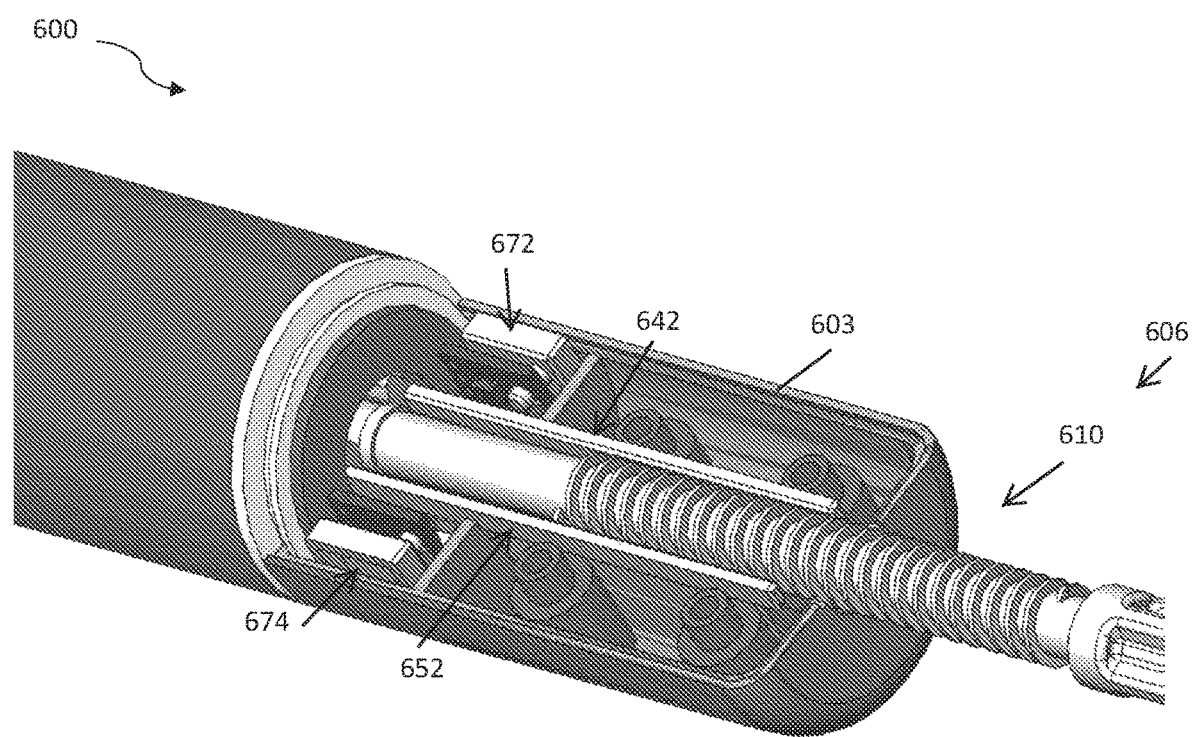
FIG. 6 is a partially exposed, side view of another radioembolization delivery device with a translational and/or rotational plunger to administer therapeutic fluid including an optical conductive rod assembly, according to one or more embodiments shown and described herein.

In an aspect, a linear encoded member is optically sensed while a device delivery arm is translated through an axial load or through a rotation. The linear encoded member is attached to a collar feature that is free to rotate about a center axis as the device delivery arm is rotated to keep the linear encoded member in a sensing area. Referring to FIG. 6, a radioembolization delivery device 600 includes a device delivery arm 606 having a threaded portion 610 and disposed in an enclosure 603 and surrounded by pair of optical rods 642, 652 of an optical conductive rod assembly including a pair of pattern sensors 672, 674 to detect optical patterns from the pair of optical rods 642, 652, such as optical high-low, alternating pattern as described with respect to the radioembolization delivery devices 400 and 500 similarly attached to respective device delivery arms 406 and 506 through non-rotational, translational clip features. In embodiments, the pattern sensors 672, 674 may be magnetic sensors configured to sense an alternating north-south pattern on the pair of rods 642, 652, and an input known start position is configured to assist the magnetic sensors from generating output signals from which to determine incremental advancement data and actual position data of the device delivery arm 606.

Figure 7:
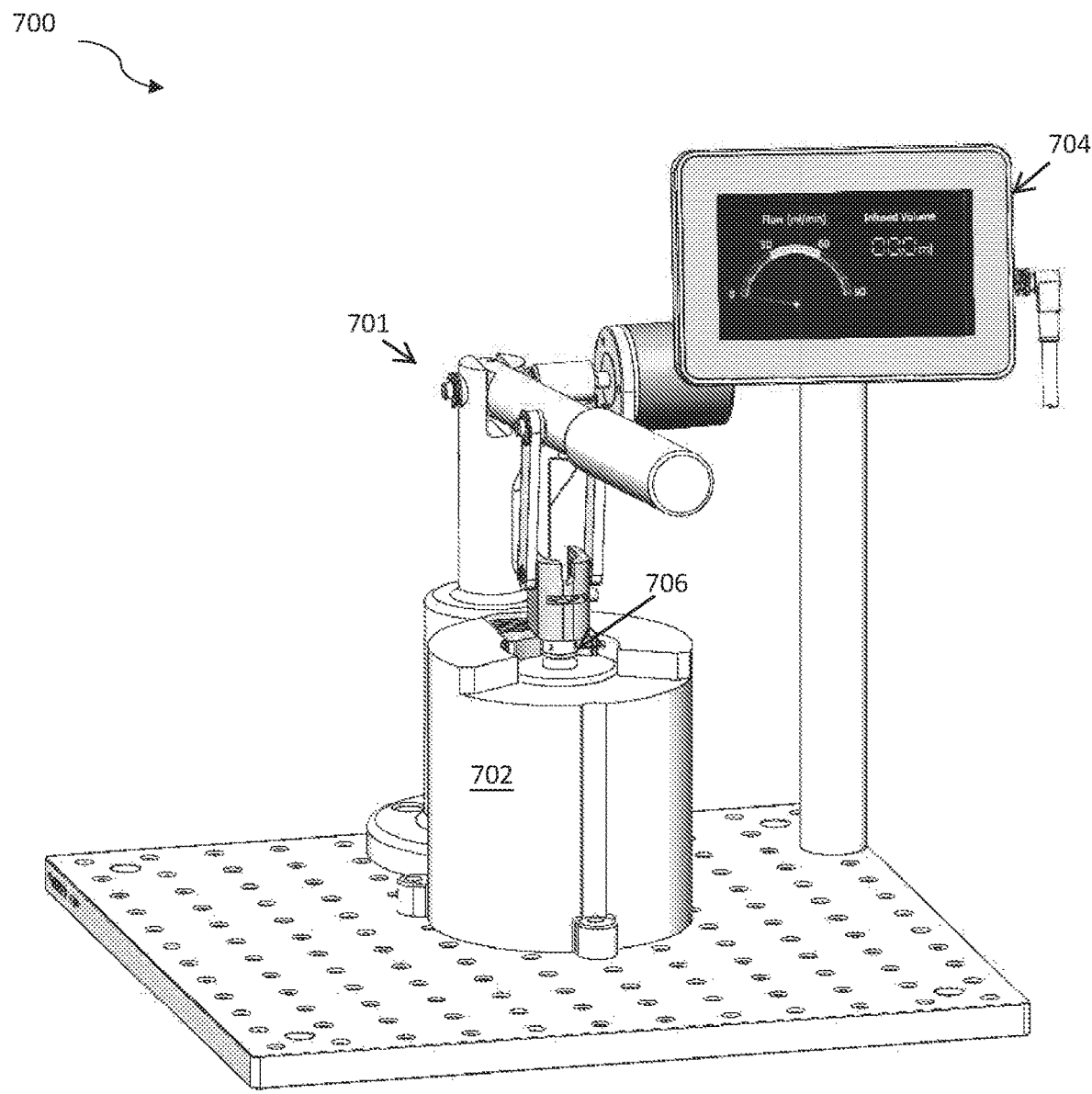
FIG. 7 is a side perspective view of a radioembolization delivery device including a lever arm assembly and a flow parameter display, according to one or more embodiments shown and described herein.

Referring to FIG. 7, a radioembolization delivery device 700 may include a lever arm assembly 701 and a flow parameter display 704 to monitor and display flow parameter information associated with sensed movement of a device delivery arm as determined and described herein. The radioembolization delivery device assembly 700 may be a delivery device as described in U.S. Provisional Pat. App. No. 62/673,632 and may include a syringe holder within a housing 702 of the radioembolization delivery device 700 to administer fluid as described in U.S. Provisional Pat. App. No. 62/673,628, each of which are incorporated by referenced herein and above. The flow parameter display 704 may be configured to display a flow rate of administered fluid (e.g., in ml/min), an amount of flow of administered fluid (e.g., as an infused volume in ml), and a direction of travel of the device delivery arm 706 (e.g., proximally or distally, wherein a distance advancement administers fluid from a syringe holder in the housing 702.

Figure 8:
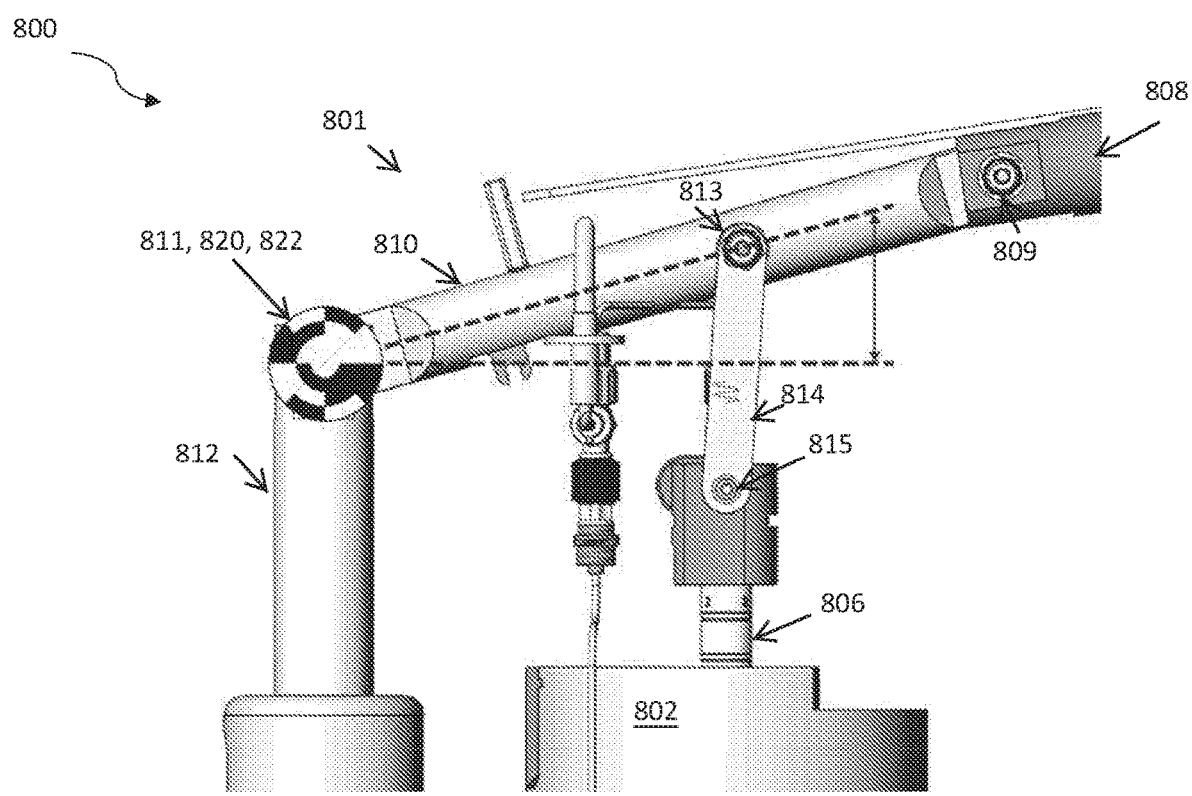
FIG. 8 is a side view of another radioembolization delivery device including a lever arm assembly and a rotary encoder assembly, according to one or more embodiments shown and described herein.

In an embodiment, a rotary quadrature encoder may be attached to a pivot point of a lever of a delivery device such that an angular displacement and direction of the lever may be sensed and the angular displacement may be converted into a linear displacement of the device delivery arm. Referring to FIG. 8, a radioembolization delivery device 800 includes a lever arm assembly 801. The lever arm assembly 801 includes a handle 808 coupled to a lever arm 810 via a pivot point 809, the lever arm 810 coupled to a base stand 812 via a pivot point 811, a link 814 coupled to the lever arm 810 via a pivot point 813, and the link 814 coupled to a device delivery arm 806 via a pivot point 815. The device delivery arm 806 is configured to proximally and distally project with respect to a housing 802 that includes a syringe holder (not shown) to administer fluid. Application of a distal, downward force on the handle 808 causes a rotation of the lever arm 810 about the pivot point 809 in a counter-clockwise direction, a distal motion of the link 814 about the pivot point 813 to drive the device delivery arm 806 distally about the pivot point 815, and a rotation of the lever arm about the pivot point 811 in a counter-clockwise direction, causing a rotation of a quadrature rotary encoder 820 including a pattern 822. A pattern sensor (not shown) is configured to sense the pattern 822 corresponding to the motion of the device delivery arm 806 in one of a distal or proximal direction with respect to the lever arm 810. An angle defined between horizontal from a center of the quadrature rotary encoder 820 and horizontal and a longitudinal axis of the lever arm 810 is used to define a distance of vertical displacement of the lever arm 810 that is associated with a translational displacement of the device delivery arm 806 with respect to the housing 802. The pattern 822 of the quadrature rotary encoder 820 may be an alternating black and white pattern to present a high-low pattern to a pattern sensor from which flow amount, flow rate, and direction of travel of the device delivery arm 806 may be generated. The radioembolization delivery device 800 including the quadrature rotary encoder 820 is thus configured to sense an angular displacement and a direction of the lever arm 810. The angular displacement may be converted to a linear displacement of the device delivery arm 806. Given a predetermined syringe diameter, a dispensed volume and flow rate may be determined based on the sensed linear displacement of the device delivery arm 806.

Figure 9:
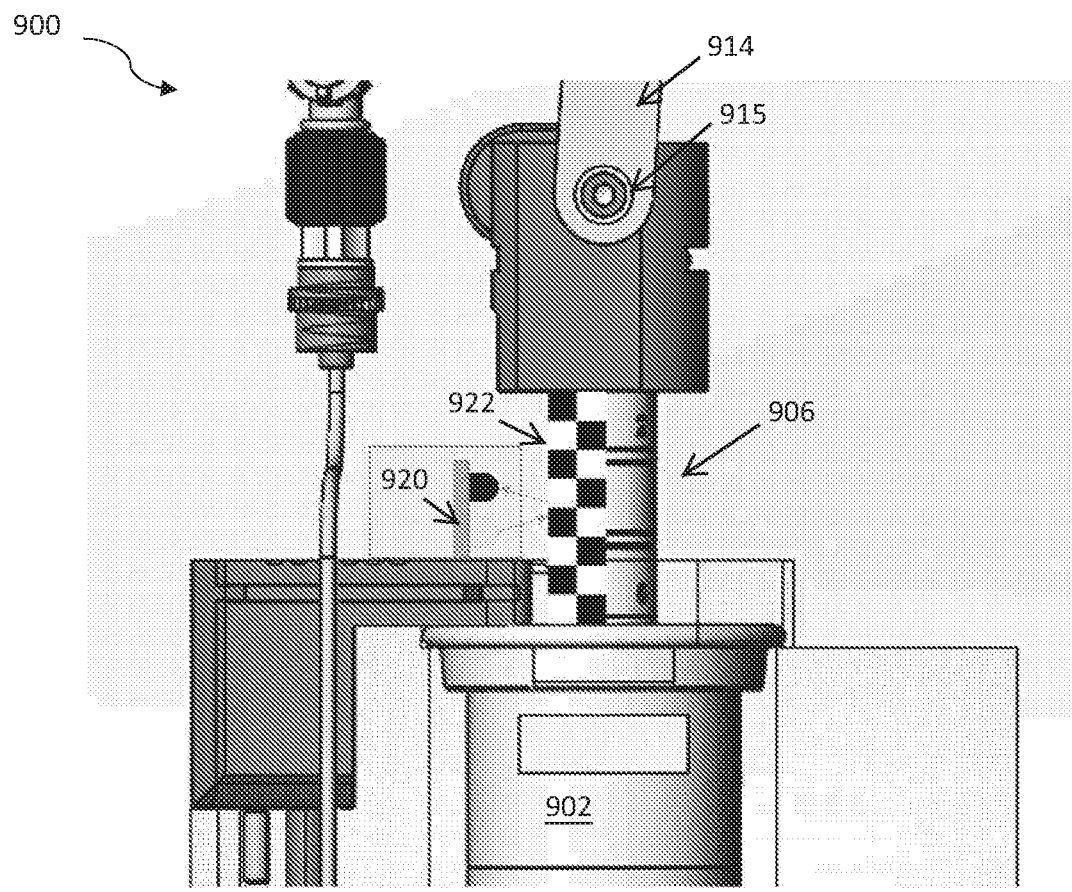
FIG. 9 is a side view of another radioembolization delivery device including a lever arm assembly and a linear encoder assembly, according to one or more embodiments shown and described herein.

According to an aspect, optical sensors may be disposed and configured proximate to the device delivery arm to act as a linear quadrature encoded to sense linear displacement and direction of the device delivery arm. Referring to FIG. 9, a radioembolization delivery device 900 includes a lever arm assembly in which a link 914 is coupled to a device delivery arm 906, similar to the lever arm assembly 801 of the radioembolization delivery device 800, to direct translational movement of the device delivery arm 906 with respect to a housing 902 within which a syringe to administered fluid is contained and may administer fluid based on a distal translation of the device delivery arm 906. The device delivery arm 906 includes a pattern 922 with an alternating high-low sequence configured for detection by an optical quadrature linear encoder 920 including an optical transmitter sensor and an optical receive sensor. The optical transmitter sensor is configured to transmit an optical signal to reflect from the pattern 922, and the optical receptor sensor is configured to receive the reflected pattern signal. It is contemplated within the scope of this disclosure that other sensors for the linear encoder 920 may be used to detect the high-low pattern 922 of the device delivery arm 906. By way of example, and not as a limitation, a Hall effect sensor, a magnetic sensor, or an electrical switch sensor as described herein may be used. The linear encoder 920 as a pattern sensor is configured to sense the pattern 922 and linear displacement and direction of the device delivery arm 906. Given a diameter of the syringe holder, a dispensed volume and flow rate of the administered fluid may be calculated based on the sensed displacement of the device delivery arm 906.

Figure 10:
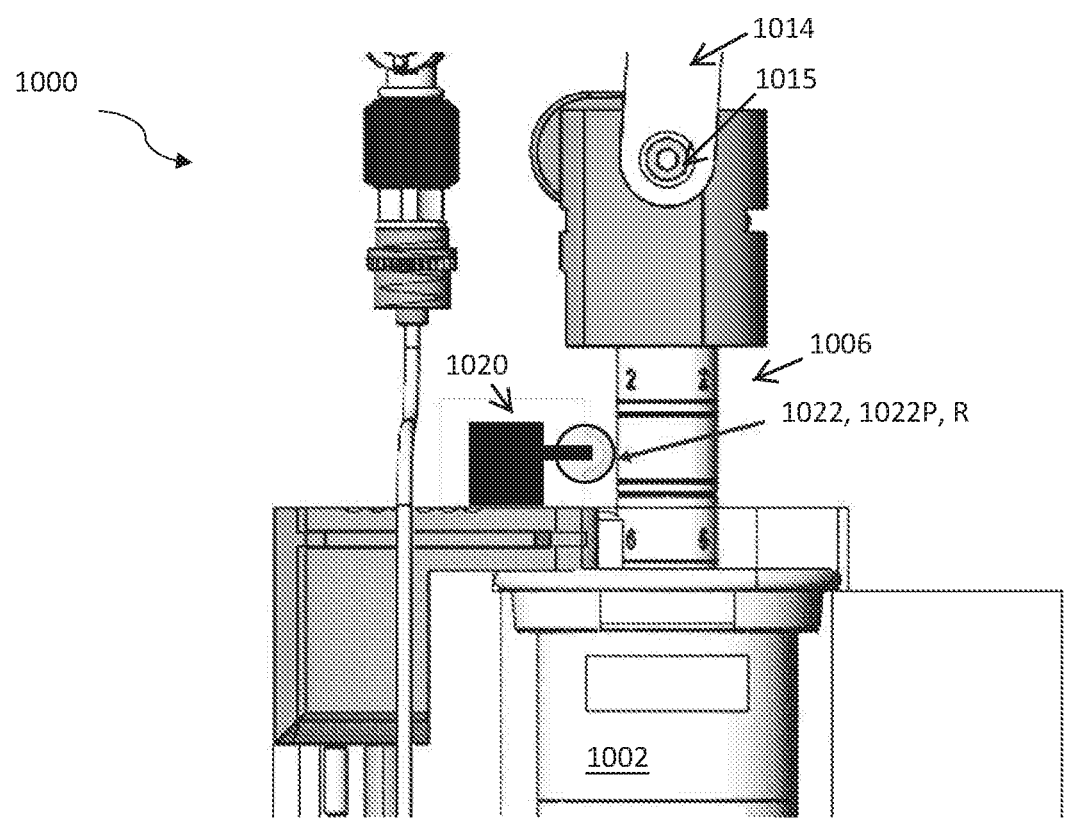
FIG. 10 is a side view of another radioembolization delivery device including a lever arm assembly and a contacting wheel rotary encoder assembly, according to one or more embodiments shown and described herein.

According to another aspect, a quadrature rotary encoder may be attached to a device delivery arm via a wheel, and a sensed angular displacement of the wheel may be converted to a linear displacement of the device delivery arm. Referring to FIG. 10, a radioembolization delivery device 1000 operates similar to the radioembolization delivery devices 800, 900 to move a link 1014 to cause a device delivery arm 1006 to rotate about a pivot point 1015 and translate in a translational direction with respect to a housing 1002 containing a syringe holder. A pattern sensor 1020 including a wheel 1022 is configured to contact a surface of the device delivery arm 1006 at a wheel contact point 1022P such that the wheel 1022 rotates clockwise in a direction of an arrow R corresponding to a distal translation of the device delivery arm 1006 toward the housing 1002. The wheel 1022 rotates counter-clock wise in a direction opposite the arrow R corresponding to a proximal translation of the device delivery arm 1006 away from the housing 1002. The wheel 1022 may include a pattern configured to be sensed by the pattern sensor 1020, which may be a quadrature rotary encoder that includes an optical, Hall effect, magnetic, or other like sensor to sense the pattern of the rotating wheel 1022. The pattern sensor 1020 is configured to thus sense the linear displacement and direction of the device delivery arm 1006. Further, given a diameter of the syringe holder, a dispensed volume and flow rate of the administered fluid from the syringe holder may be calculated based on the linear displacement and direction information of the device delivery arm 1006.

Figure 11:
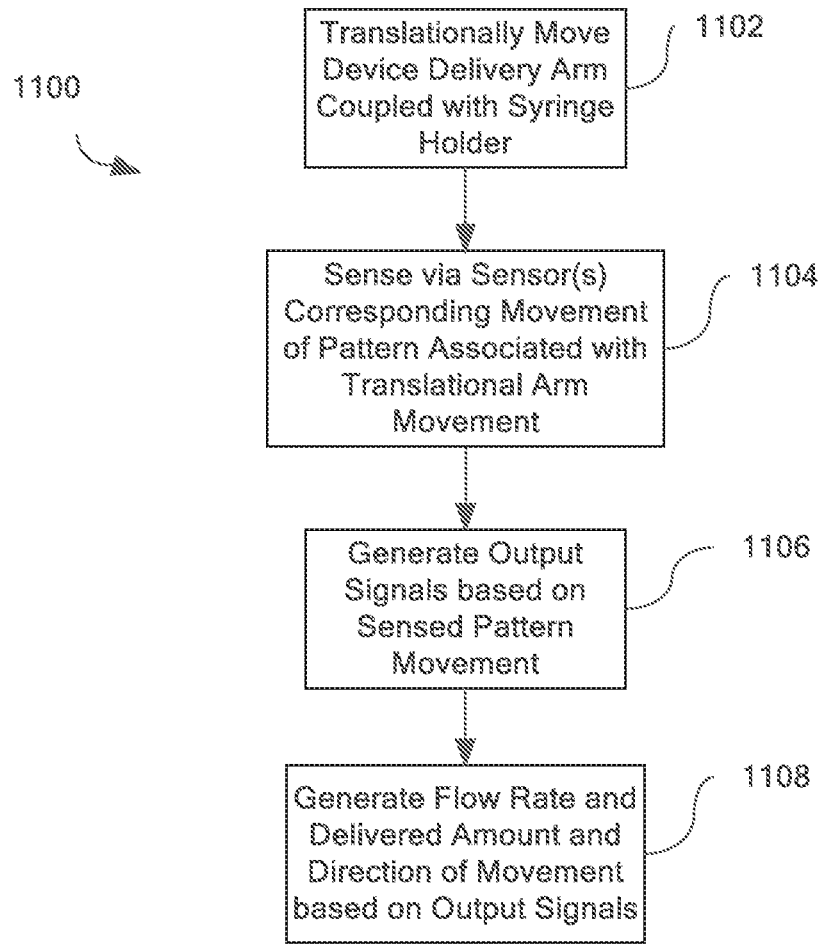
FIG. 11 is a flow chart of a process utilizing the devices of FIGS. 1-10, according to one or more embodiments shown and described herein.

Referring to FIG. 11, a flow chart of a process 1100 is shown that utilizes the radioembolization delivery devices 100, 200, 300, 400, 500, 600, 700, 800, 900, 1000 of FIGS. 1-10 to determine flow rate of administered fluid, flow amount, and a direction of travel of a respective device delivery arm as described herein. The process 1100 for determination of flow parameters of administered fluid from a radioembolization delivery device 100, 200, 300, 400, 500, 600, 700, 800, 900, 1000 may include, in block 1102, translationally moving a respective device delivery arm 106, 206, 306, 406, 506, 706, 806, 906, 1006 of the radioembolization delivery device 100, 200, 300, 400, 500, 600, 700, 800, 900, 1000 in a translational direction. The respective device delivery arm 106, 206, 306, 406, 506, 706, 806, 906, 1006 may be coupled to a syringe holder such that movement in the translational direction one of proximally or distally advances the syringe holder. A distal advancement, for example, may cause the syringe holder to administer the therapeutic fluid. Thus, a distal advancement of the syringe holder may be configured to administer the fluid from the radioembolization delivery device 100, 200, 300, 400, 500, 600, 700, 800, 900, 1000 into a blood vessel.

In embodiments, the translational direction is one of a first direction along a longitudinal axis LA of the device delivery arm 106, 206, 306, 406, 506, 706, 806, 906, 1006 or a second direction that is opposite the first direction. The first direction may be one of a proximal advancement and a distal advancement along the longitudinal axis LA corresponding to a proximal or distance advancement of the syringe holder, and the second direction may be the other of the proximal advancement or the distal advancement. Further, the device delivery arm 106, 206, 306, 406, 506, 706, 806, 906, 1006 may be rotated about the longitudinal axis LA of the device delivery arm 106, 206, 306, 406, 506, 706, 806, 906, 1006 when translationally moving the device delivery arm 106, 206, 306, 406, 506, 706, 806, 906, 1006 in the translational direction along the longitudinal axis LA.

In block 1104, a corresponding movement of a pattern associated with the translational device delivery arm movement is sensed, via one or more pattern sensors as described herein with respect to FIGS. 1-10, as a sensed pattern movement. In embodiments, and as described herein, the one or more pattern sensors may include at least one of an optical sensor, a Hall effect sensor, a magnetic sensor, or a switch-based sensor configured to sense a corresponding alternating high-low pattern associated with the device delivery arm 106, 206, 306, 406, 506, 706, 806, 906, 1006 and including a corresponding optical, electromagnetic, magnetic, or switch pattern.

In block 1106, one or more output signals are generated, via the one or more pattern sensors, based on the sensed pattern movement. Referring to FIGS. 1-10, as described herein and above, the one or more pattern sensors are configured to detect a pattern associated with a translational motion of a respective device delivery arm. By way of example, and not as a limitation, and referring to FIGS. 1A-1B, the one or more pattern sensors may include a gear assembly 112 configured to detect a ring pattern of a ring portion 108 on the device delivery arm 106 of a radioembolization delivery device 100. Referring to FIGS. 2A-2B, the one or more pattern sensors 222, 224 may include a ring assembly configured to detect the pattern comprising a ring pattern of a ring portion 208 on the device delivery arm 206. The ring assembly may include a pair of Hall effect sensors, and the ring pattern may include one of magnets or ferrous objects embedded in the device delivery arm. Alternatively, the ring assembly may include a pair of optical sensors, and the ring pattern may include at least two different reflective surface types for detection by the pair of optical sensors.

Referring to FIGS. 3A-3B, the one or more pattern sensors may include an omni wheel assembly 328 configured to detect the pattern including a thread pattern of a threaded portion 310 on the device delivery arm 306. Referring to FIGS. 4A-4C, the one or more pattern sensors may include a conductive rod assembly including a pair of conductive rods 442, 452 and configured to detect the pattern based on alternating switch patterns 444, 454 disposed on the pair of conductive rods 442, 452 attached to the device delivery arm 406. Referring to FIGS. 5A-5B, the one or more pattern sensors may include a rack and pinion rod assembly 560 configured to detect the pattern based on a rack pattern on at least one rack rod 542 attached to the device delivery arm 506. Referring to FIG. 6, the one or more pattern sensors may include an optical conductive rod assembly including a pair of pattern sensors 672, 652 configured to detect the pattern based on an optical pattern of at least one conductive optical rod 642, 652 attached to the device delivery arm 606.

Referring to FIG. 8, the one or more pattern sensors may include a rotary encoder assembly configured to detect the pattern 822 from a rotation of a quadrature rotary encoder 820 based on a pivot around a pivot joint 811 corresponding to a translation of the device delivery arm 806. Referring to FIG. 9, the one or more pattern sensors may include an optical linear encoder assembly including the optical quadrature linear encoder 920 configured to detect the pattern 922 as an alternating optical high-low pattern disposed on the device delivery arm 906. Referring to FIG. 10, the one or more pattern sensors 1020 may include a rotary encoder assembly including a wheel 1022. The rotary encoder assembly may include a wheel encoder as the wheel 1022 configured to contact a surface of the device delivery arm 1006. When the device delivery moves in a translation in the translational direction, the wheel encoder including the pattern is configured to rotate, and the one or more pattern sensors 1020 are configured to detect the pattern on the wheel encoder (e.g., the wheel 1022) corresponding to the translation of the device delivery arm 1006.

In block 1108, a flow rate of the administered fluid, a flow amount of the administered fluid, and the translational direction of movement of the device delivery arm 106, 206, 306, 406, 506, 706, 806, 906, 1006 with respect to the syringe holder, for a which a diameter is known, is generated, via processor, based on the one or more output signals. In embodiments, at least one of the flow rate of the administered fluid, the flow amount of the administered fluid, or the direction of movement of the device delivery arm 106, 206, 306, 406, 506, 706, 806, 906, 1006 may be displayed on a display 704 communicatively coupled to the radioembolization delivery device 100, 200, 300, 400, 500, 600, 700, 800, 900, 1000.

Figure 12:
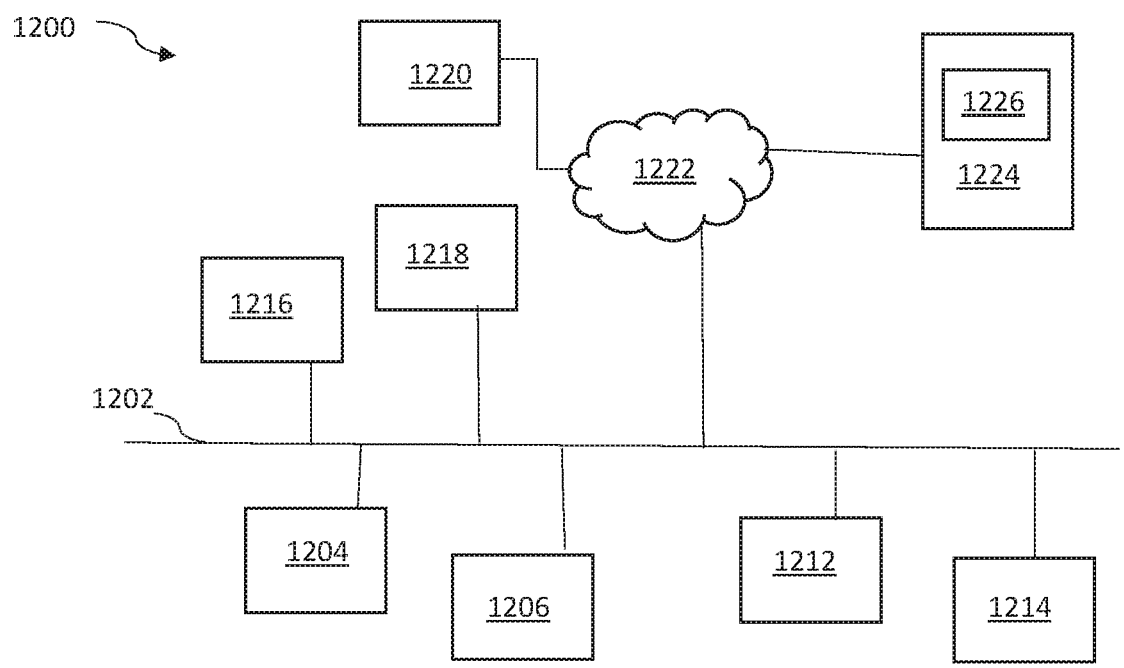
FIG. 12 schematically illustrates a system for implementing computer and software based methods to apply a flow parameter determination process with the devices of FIGS. 1-10, according to one or more embodiments shown and described herein.

Referring to FIG. 12, a system 1200 for implementing a computer and software-based method to utilize the delivery device embodiments described herein to determine flow parameters of administered fluid from such radioembolization delivery devices 1224 is illustrated as being implemented along with using a graphical user interface (GUI) 1226 communicatively coupled to radioembolization delivery devices 1224 to display the one or more flow parameters, for example. The system 1200 includes a communication path 1202, one or more processors 1204, a memory component 1206, a pattern tool 1212, a storage or database 1214, a pattern sensor 1216 configured to sense a pattern from the pattern tool 1212 as described herein, a network interface hardware 1218, a network 1222, a server 1220 that may include a cloud-based server, and a radioembolization delivery device 1224. The radioembolization delivery device 1224 may be any of the embodiments of devices 100, 200, 300, 400, 500, 600, 700, 800, 900, 1000 described herein and/or the delivery devices described in U.S. Provisional Pat. App. No. 62/673,628 or U.S. Provisional Pat. App. No. 62/673,632, each of which incorporated by reference herein and above. The various components of the system 1200 and the interaction thereof will be described in detail below. The pattern sensor 1216 may be, for example, one or more of an optical sensor, a Hall effect sensor, a magnetic sensor, a switch-based sensor, an inductive sensor, a capacitive sensor, a wireless Bluetooth® sensor, and/or the like as described herein.

In some embodiments, the system 1200 is implemented using a wide area network (WAN) or network 1222, such as an intranet or the Internet. The radioembolization delivery device 1224 may include digital systems and other devices permitting connection to and navigation of the network. The lines depicted in FIG. 12 indicate communication rather than physical connections between the various components.

As noted above, the system 1200 includes the communication path 1202. The communication path 1202 may be formed from any medium that is capable of transmitting a signal such as, for example, conductive wires, conductive traces, optical waveguides, or the like, or from a combination of mediums capable of transmitting signals. The communication path 1202 communicatively couples the various components of the system 1200. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 1200 includes the processor 1204. The processor 1204 can be any device capable of executing machine readable instructions. Accordingly, the processor 1204 may be a controller, an integrated circuit, a microchip, a computer, or any other computing device. The processor 1204 is communicatively coupled to the other components of the system 1200 by the communication path 1202. Accordingly, the communication path 1202 may communicatively couple any number of processors with one another, and allow the modules coupled to the communication path 1202 to operate in a distributed computing environment. Specifically, each of the modules can operate as a node that may send and/or receive data.

As noted above, the system 1200 includes the memory component 1206 which is coupled to the communication path 1202 and communicatively coupled to the processor 1204. The memory component 1206 may be a non-transitory computer readable medium or non-transitory computer readable memory and may be configured as a nonvolatile computer readable medium. The memory component 1206 may comprise RAM, ROM, flash memories, hard drives, or any device capable of storing machine readable instructions such that the machine readable instructions can be accessed and executed by the processor 1204. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 1206. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

Still referring to FIG. 12, as noted above, the system 1200 comprises the display such as a GUI 1226 on a screen communicatively coupled to the one or more radioembolization delivery devices 1224 for providing visual output such as, for example, information, graphical reports, messages, or a combination thereof. The display on the screen is coupled to the communication path 1202 and communicatively coupled to the processor 1204. Accordingly, the communication path 1202 communicatively couples the display to other modules of the system 1200. The display can include any medium capable of transmitting an optical output such as, for example, a cathode ray tube, light emitting diodes, a liquid crystal display, a plasma display, or the like. Additionally, it is noted that the display can include at least one of the processor 1204 and the memory component 1206. While the system 1200 is illustrated as a single, integrated system in FIG. 12, in other embodiments, the systems can be independent systems.

The system 1200 may comprise the pattern sensor 1216 to sense a pattern from the pattern tool 1212, as per one or more of the embodiments described herein, to transmit pattern signal information used to compute one or more flow parameters based on the pattern signal information. As will be described in further detail below, the processor 1204 may process the input signals received from the system modules and/or extract information from such signals. For example, in embodiments, the processor 1204 may execute instructions stored in the memory component 1206 to implement the processes described herein.

The system 1200 includes the network interface hardware 1218 for communicatively coupling the system 1200 with a computer network such as network 1222. The network interface hardware 1218 is coupled to the communication path 1202 such that the communication path 1202 communicatively couples the network interface hardware 1218 to other modules of the system 1200. The network interface hardware 1218 can be any device capable of transmitting and/or receiving data via a wireless network. Accordingly, the network interface hardware 1218 can include a communication transceiver for sending and/or receiving data according to any wireless communication standard. For example, the network interface hardware 1218 can include a chipset (e.g., antenna, processors, machine readable instructions, etc.) to communicate over wired and/or wireless computer networks such as, for example, wireless fidelity (Wi-Fi), WiMax, Bluetooth®, IrDA, Wireless USB, Z-Wave, ZigBee, or the like.

Still referring to FIG. 12, data from various applications running on programs associated with the radioembolization delivery devices 1224 can be provided to the system 1200 via the network interface hardware 1218. The radioembolization delivery devices 1224 can be any device having hardware (e.g., chipsets, processors, memory, etc.) for communicatively coupling with the network interface hardware 1218 and a network 1222.

The network 1222 can include any wired and/or wireless network such as, for example, wide area networks, metropolitan area networks, the Internet, an Intranet, satellite networks, or the like. Accordingly, the network 1222 can be utilized as a wireless access point to access one or more servers (e.g., a server 1220). The server 1220 and any additional servers generally include processors, memory, and chipset for delivering resources via the network 1222. Resources can include providing, for example, processing, storage, software, and information from the server 1220 to the system 1200 via the network 1222. Additionally, it is noted that the server 1220 and any additional servers can share resources with one another over the network 1222 such as, for example, via the wired portion of the network, the wireless portion of the network, or combinations thereof.

In embodiments described herein, one or more pattern sensors in radioembolization delivery devices disposed away from a fluid administration path are used to record position of a device delivery arm and motion to continuously calculate and determine an infused volume and flow rate of a therapeutic fluid with sub-mL/min resolution and to dynamically display the information in real-time. The clinical may then be able to use the displayed information to dynamically tune the administration rate and keep the rate within a desired range throughout the procedure and to keep track of the total infused volume, all of which provide for a more efficient and safe procedure. Indeed, the systems and methods described herein allow for a recordation of flow rate and infused volume of therapeutic fluid and displaying of both parameters dynamically during a procedure. The pattern sensors described herein may be reusable sensors including accompanying electronics and a display integrated with a delivery device and disposed away from a fluid delivery path for the therapeutic fluid. In embodiments, an electro-mechanically driven administration procedure may involve an automatic determination of flow rate and infused volume based on driving and sensing information related to motor speed, direction, and frequency to control the device delivery arm coupled to the syringe holder to deliver the therapeutic fluid. A system to control the delivery devices described herein may be automatically, partially automatically, or manual controlled by a clinician through, for example, a joystick or button to control start, pause, and/or stop injection operations.

The embodiments described herein employ one or more pattern sensors to sense an angular or linear displacement of one or more components used to delivery Y90 microspheres during a radioembolization procedure. The sensed information may then be used to determine volumetric flow and flow rate of administered therapeutic fluid during the procedure. Different methods to sense relative displacement may be used with respect to the pattern sensors, including, but not limited to, angular and linear encoders, inductive proximity sensors, optical proximity sensors, capacitive proximity sensors, ultrasonic proximity sensor, and/or mechanical switches. Further, in addition to use of pattern sensors to sense flow as described herein, other sensors may be used such as a radioactive dosimeter to monitor bead concentration and potential leakage, a pressure sensor to monitor and report fluid pressure, and a temperature sensor to monitor and report fluid or ambient temperature during the procedure.

Items Listing

Item 1. A method for determination of flow parameters of administered fluid from a radioembolization delivery device may include translationally moving a device delivery arm of the radioembolization delivery device in a translational direction, wherein the device delivery arm is coupled to a syringe holder such that movement in the translational direction one of proximally or distally advances the syringe holder, and sensing, via one or more pattern sensors, a corresponding movement of a pattern associated with the translational device delivery arm movement as a sensed pattern movement. The method may further include generating, via the one or more pattern sensors, one or more output signals based on the sensed pattern movement, and generating, via a processor, at least one of a flow rate of the administered fluid, a flow amount of the administered fluid, or the translational direction of movement of the device delivery arm with respect to the syringe holder based on the one or more output signals.

Item 2. The method of item 1, further including displaying at least one of the flow rate of the administered fluid, the flow amount of the administered fluid, or the direction of movement of the device delivery arm on a display communicatively coupled to the radioembolization delivery device.

Item 3. The method of items 1 or 2, wherein a distal advancement of the syringe holder is configured to administer the fluid from the radioembolization delivery device into a blood vessel.

Item 4. The method of any of items 1 to 3, wherein the translational direction is one of a first direction along a longitudinal axis of the device delivery arm or a second direction; the second direction is opposite the first direction; the first direction is one of a proximal advancement and a distal advancement along the longitudinal axis corresponding to a proximal or distance advancement of the syringe holder; and the second direction is the other of the proximal advancement or the distal advancement.

Item 5. The method of any of items 1 to 4, further including rotating the device delivery arm about a longitudinal axis of the device delivery arm when translationally moving the device delivery arm in the translational direction along the longitudinal axis.

Item 6. The method of any of items 1 to 6, wherein the one or more pattern sensors include at least one of an optical sensor, a Hall effect sensor, a magnetic sensor, or a switch-based sensor configured to sense a corresponding alternating high-low pattern associated with the device delivery arm and comprising a corresponding optical, electromagnetic, magnetic, or switch pattern.

Item 7. The method of any of items 1 to 6, wherein the one or more pattern sensors include a gear assembly configured to detect a ring pattern on the device delivery arm.

Item 8. The method of any of items 1 to 6, wherein the one or more pattern sensors comprise a ring assembly configured to detect the pattern including a ring pattern on the device delivery arm.

Item 9. The method of item 8, wherein the ring assembly includes a pair of Hall effect sensors and the ring pattern includes one of magnets or ferrous objects embedded in the device delivery arm.

Item 10. The method of item 8, wherein the ring assembly includes a pair of optical sensors and the ring pattern includes at least two different reflective surface types for detection by the pair of optical sensors.

Item 11. The method of any of items 1 to 6, wherein the one or more pattern sensors include an omni wheel assembly configured to detect the pattern including a thread pattern on the device delivery arm.

Item 12. The method of any of items 1 to 6, wherein the one or more pattern sensors include a conductive rod assembly configured to detect the pattern based on alternating switch patterns disposed on a pair of conductive rods attached to the device delivery arm.

Item 13. The method of any of items 1 to 6, wherein the one or more pattern sensors include a rack and pinion rod assembly configured to detect the pattern based on a rack pattern on at least one rack rod attached to the device delivery arm.

Item 14. The method of any of items 1 to 6, wherein the one or more pattern sensors include an optical conductive rod assembly configured to detect the pattern based on an optical pattern of at least one conductive optical rod attached to the device delivery arm.

Item 15. The method of any of items 1 to 6, wherein the one or more pattern sensors include a rotary encoder assembly configured to detect the pattern based on a pivot around a pivot joint corresponding to a translation of the device delivery arm.

Item 16. The method of any of items 1 to 6, wherein the one or more pattern sensors include an optical linear encoder assembly configured to detect the pattern as an alternating optical high-low pattern disposed on the device delivery arm.

Item 17. The method of any of items 1 to 6, wherein the one or more pattern sensors include a rotary encoder assembly including a wheel encoder configured to contact a surface of the device delivery arm such that when the device delivery arm moves in a translation in the translational direction, the wheel encoder including the pattern is configured to rotate, and the one or more pattern sensors are configured to detect the pattern on the wheel encoder corresponding to the translation of the device delivery arm.

Item 18. A system for determination of flow parameters of administered fluid from a radioembolization delivery device may include: a radioembolization delivery device including a device delivery arm coupled to a syringe holder, a pattern assembly, and one or more pattern sensors configured to detect the pattern assembly based on movement of the pattern assembly, and the device delivery arm configured to move in a translational direction to one of proximally or distally advance the syringe holder; and a processor communicatively coupled to the radioembolization delivery device and a non-transitory computer storage medium. The non-transitory computer storage medium may store instructions that, when executed by the processor, cause the processor to: monitor translational movement of the device delivery arm of the radioembolization delivery device in the translational direction; sense, via the one or more pattern sensors, a corresponding movement of the pattern assembly associated with the translational device delivery arm movement as a sensed pattern movement; generate, via the one or more pattern sensors, one or more output signals based on the sensed pattern movement; and generate at least one of a flow rate of the administered fluid, a flow amount of the administered fluid, or a direction of movement of the device delivery arm with respect to the syringe holder based on the one or more output signals.

Item 19. The system of item 18, further including instructions that, when executed by the processor, cause the processor to display at least one of the flow rate of the administered fluid, the flow amount of the administered fluid, or the direction of movement of the device delivery arm on a display communicatively coupled to the radioembolization delivery device.

Item 20. The system of item 18 or item 19, wherein a distal advancement of the syringe holder is configured to administer the fluid from the radioembolization delivery device into a blood vessel.

Item 21. The system of any of items 18 to 20, wherein: the translational direction is one of a first direction along a longitudinal axis of the device delivery arm or a second direction; the second direction is opposite the first direction; the first direction is one of a proximal advancement and a distal advancement along the longitudinal axis corresponding to a proximal or distance advancement of the syringe holder; and the second direction is the other of the proximal advancement or the distal advancement.

Item 22. The system of any of items 18 to 21, further including instructions that, when executed by the processor, cause the processor to monitor rotation of the device delivery arm about a longitudinal axis of the device delivery arm when the device delivery arm is being translationally moved in the translational direction along the longitudinal axis.

Item 23. The system of any of items 18 to 22, wherein the one or more pattern sensors include at least one of an optical sensor, a Hall effect sensor, a magnetic sensor, or a switch-based sensor configured to sense a corresponding alternating high-low pattern associated with the device delivery arm and including a corresponding optical, electromagnetic, magnetic, or switch pattern.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A method for determination of flow parameters of administered fluid from a radioembolization delivery device, the method comprising:
   translationally moving a device delivery arm of the radioembolization delivery device in a translational direction, wherein the device delivery arm is coupled to a syringe holder in a housing of the radioembolization device such that movement in the translational direction proximally or distally advances the syringe holder;
   sensing, via one or more pattern sensors, a corresponding movement of a pattern associated with the movement of the translational device delivery arm coupled to the syringe holder as a sensed pattern movement;
   generating, via the one or more pattern sensors, one or more output signals based on the sensed pattern movement; and
   generating, via a processor, at least one of a flow rate of the administered fluid, a flow amount of the administered fluid, or the translational direction of movement of the device delivery arm with respect to the syringe holder based on the one or more output signals.

2. The method of claim 1, further comprising displaying at least one of the flow rate of the administered fluid, the flow amount of the administered fluid, or the direction of movement of the device delivery arm on a display communicatively coupled to the radioembolization delivery device.

3. The method of claim 1, wherein a distal advancement of the syringe holder is configured to administer the fluid from the radioembolization delivery device into a blood vessel.

4. The method of claim 1, wherein:
   the translational direction is one of a first direction along a longitudinal axis of the device delivery arm or a second direction;
   the second direction is opposite the first direction;
   the first direction is one of a proximal advancement and a distal advancement along the longitudinal axis corresponding to a proximal or distal advancement of the syringe holder; and the second direction is one other of the proximal advancement or the distal advancement.

5. The method of claim 1, wherein a rotation of the device delivery arm about a longitudinal axis of the device delivery arm effects the translationally moving the device delivery arm in the translational direction along the longitudinal axis.

6. The method of claim 1, wherein the one or more pattern sensors comprise at least one of an optical sensor, a Hall effect sensor, a magnetic sensor, or a switch-based sensor configured to sense a corresponding alternating high-low pattern associated with the device delivery arm and comprising a corresponding optical, electromagnetic, magnetic, or switch pattern.

7. The method of claim 1, wherein the one or more pattern sensors comprise a gear assembly configured to detect a ring pattern on the device delivery arm.

8. The method of claim 1, wherein the one or more pattern sensors comprise a ring assembly configured to detect the pattern, said pattern comprising a ring pattern on the device delivery arm.

9. The method of claim 8, wherein the ring assembly comprises a pair of Hall effect sensors and the ring pattern comprises one of magnets or ferrous objects embedded in the device delivery arm.

10. The method of claim 8, wherein the ring assembly comprises a pair of optical sensors and the ring pattern comprises at least two different reflective surface types for detection by the pair of optical sensors.

11. The method of claim 1, wherein the one or more pattern sensors comprise an omni wheel assembly configured to detect the pattern comprising a thread pattern on the device delivery arm.

12. The method of claim 1, wherein the one or more pattern sensors comprise a conductive rod assembly configured to detect the pattern based on alternating switch patterns disposed on a pair of conductive rods attached to the device delivery arm.

13. The method of claim 1, wherein the one or more pattern sensors comprise a rack and pinion rod assembly configured to detect the pattern based on a rack pattern on at least one rack rod attached to the device delivery arm.

14. The method of claim 1, wherein the one or more pattern sensors comprise an optical conductive rod assembly configured to detect the pattern based on an optical pattern of at least one conductive optical rod attached to the device delivery arm.

15. The method of claim 1, wherein the one or more pattern sensors comprise a rotary encoder assembly configured to detect the pattern based on a pivot around a pivot joint corresponding to the translation of the device delivery arm.

16. The method of claim 1, wherein the one or more pattern sensors comprise an optical linear encoder assembly configured to detect the pattern, said pattern being an alternating optical high-low pattern disposed on the device delivery arm.

17. The method of claim 1, wherein the one or more pattern sensors comprise a rotary encoder assembly comprising a wheel encoder configured to contact a surface of the device delivery arm such that when the device delivery arm moves in a translation in the translational direction, the wheel encoder is configured to rotate and comprises the pattern, and the one or more pattern sensors are configured to detect the pattern on the wheel encoder corresponding to the translation of the device delivery arm.

18. A system for determination of flow parameters of administered fluid from a radioembolization delivery device, the system comprising:
the radioembolization delivery device including a device delivery arm coupled to a syringe holder in a housing of the radioembolization device, a pattern assembly, and one or more pattern sensors configured to detect the pattern assembly based on movement of the pattern assembly, and the device delivery arm configured to move in a translational direction to one of proximally or distally advance the syringe holder; and
a processor communicatively coupled to the radioembolization delivery device and a non-transitory computer storage medium, wherein the non-transitory computer storage medium stores instructions that, when executed by the processor, cause the processor to:
monitor translational movement of the device delivery arm of the radioembolization delivery device in the translational direction;
sense, via the one or more pattern sensors, a corresponding movement of the pattern assembly associated with the movement of the translational device delivery arm coupled to the syringe holder as a sensed pattern movement;
generate, via the one or more pattern sensors, one or more output signals based on the sensed pattern movement; and
generate at least one of a flow rate of the administered fluid, a flow amount of the administered fluid, or a direction of movement of the device delivery arm with respect to the syringe holder based on the one or more output signals.

19. The system of claim 18, further comprising instructions that, when executed by the processor, cause the processor to display at least one of the flow rate of the administered fluid, the flow amount of the administered fluid, or the direction of movement of the device delivery arm on a display communicatively coupled to the radioembolization delivery device.

20. The system of claim 18, wherein a distal advancement of the syringe holder is configured to administer the fluid from the radioembolization delivery device into a blood vessel.

21. The system of claim 18, wherein:
the translational direction is one of a first direction along a longitudinal axis of the device delivery arm or a second direction;
the second direction is opposite the first direction;
the first direction is one of a proximal advancement and a distal advancement along the longitudinal axis corresponding to a proximal or distal advancement of the syringe holder; and
the second direction is the other of the proximal advancement or the distal advancement.

22. The system of claim 18, further comprising instructions that, when executed by the processor, cause the processor to monitor rotation of the device delivery arm about a longitudinal axis of the device delivery arm when the device delivery arm is being translationally moved in the translational direction along the longitudinal axis.

23. The system of claim 18, wherein the one or more pattern sensors comprise at least one of an optical sensor, a Hall effect sensor, a magnetic sensor, or a switch-based sensor configured to sense a corresponding alternating high-low pattern associated with the device delivery arm and comprising a corresponding optical, electromagnetic, magnetic, or switch pattern.

* * * * *